(12) United States Patent
Kurosawa et al.

(10) Patent No.: US 9,139,855 B2
(45) Date of Patent: *Sep. 22, 2015

(54) PRODUCTION OF TRIACYLGLYCERIDES FROM RENEWABLE BIOMASS USING OLEAGINOUS MICROORGANISMS

(71) Applicant: Massachusetts Institute of Technology, Cambridge, MA (US)

(72) Inventors: Kazuhiko Kurosawa, Somerville, MA (US); Anthony John Sinskey, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,897

(22) Filed: Oct. 19, 2012

(65) Prior Publication Data

US 2013/0137887 A1 May 30, 2013

Related U.S. Application Data

(60) Provisional application No. 61/548,971, filed on Oct. 19, 2011, provisional application No. 61/558,256, filed on Nov. 10, 2011.

(51) Int. Cl.
*C12P 7/64* (2006.01)
*C12P 19/14* (2006.01)
*C12R 1/01* (2006.01)

(52) U.S. Cl.
CPC ............ *C12P 7/6463* (2013.01); *C12P 19/14* (2013.01); *C12R 1/01* (2013.01)

(58) Field of Classification Search
CPC ...... C12P 7/6463; C12P 7/649; C12P 7/6409; C12P 7/6436; C12P 7/64; C12P 7/20; C12P 7/02; C12P 7/10; C12N 9/90; C12N 1/22; C12N 9/52

See application file for complete search history.

(56) References Cited

U.S. PATENT DOCUMENTS 8,679,782 B2 * 3/2014 Sinskey et al. ............... 435/69.1
2012/0171735 A1 7/2012 Sinskey et al.

FOREIGN PATENT DOCUMENTS

WO WO 2010/147642 A1 12/2010

OTHER PUBLICATIONS

Holder J.W. et al., Comparative and Functional Genomics of Rhodococcus opacus PD630 for Biofuels Development, PLOS Genetics, Sep. 8, 2011, vol. 7, No. 9, pp. 1-18.*
Waltermann M. et al., Rhodococcus opacus strain PD630 as a new source of high-value single-cell oil? Isolation and characterization of triacylglycerols and other storage lipids, Microbiology, 2000, vol. 146, pp. 1143-1149.*
Xiong X. et al., Engineering of a Xylose Metabolic Pathway in Rhodococcus Strains, Applied and Environmental Microbiology, Aug. 2012, vol. 78, No. 16, pp. 5483-5491.*
Kurosawa K., Triacylglycerol production from corn stover silage using a xylose-fermenting Rhodococcus opacus strain, Poster presented at the AIChE Annual Meeting on Oct. 18, 2011, pp. 1-3.*
Energy futures—"Engineering fat-making bacteria: a road to plentiful biodiesel", a research report published by MIT Energy Initiative, Spring 2010, pp. 1-45.*
Kurosawa et al., High-cell-density batch fermentation of Rhodococcus opacus PD630 using a high glucose concentration for triacylglycerol production. *J of Biotech*. Jun. 2010;147(3-4):212-8. Epub Apr. 20, 2010.

* cited by examiner

*Primary Examiner* — Satyendra Singh
(74) *Attorney, Agent, or Firm* — Wolf, Greenfield & Sacks, P.C.

(57) ABSTRACT

The embodiments disclosed herein relate to bacterial cell production of triacylglycerides from renewable biomass resources.

22 Claims, 15 Drawing Sheets

PRODUCTION OF TRIACYLGLYCERIDES FROM RENEWABLE BIOMASS USING OLEAGINOUS MICROORGANISMS

RELATED APPLICATIONS

This application claims the benefit under 35 U.S.C. §119(e) of U.S. provisional application No. 61/548,971, filed Oct. 19, 2011, and of U.S. provisional application No. 61/558,256, filed Nov. 10, 2011, each of which is incorporated by reference herein in its entirety.

FEDERALLY SPONSORED RESEARCH

This invention was made with government support under Grant No. HR0011-10-C-0187 awarded by the Defense Advanced Research Projects Agency. The government has certain rights in this invention.

FIELD OF THE INVENTION

This invention relates to bacterial cell production of high titers of triacylglycerides from renewable biomass resources.

BACKGROUND OF INVENTION

Oleaginous microorganisms, such as *Rhodococcus*, are capable of accumulating a large amount of triacylglycerides (TAGs) converted to liquid biofuels such as gasoline, kerosene, jet, and diesel fuels. These bacterial cells, however, are not naturally capable of metabolizing xylose to produce TAGs.

SUMMARY OF INVENTION

Provided herein are methods of producing triacylglycerides from renewable biomass comprising culturing at least one (e.g., one or more) xylose-fermenting *Rhodococcus* bacterial strain. In some embodiments, the renewable biomass comprises xylose, xylan, xylose polymer or a combination thereof.

In some aspects, provided herein are methods comprising culturing, in culture medium supplemented with xylose, a population of *Rhodococcus* bacterial cells that metabolize (or ferment) xylose for a time sufficient for the bacterial cells to produce triacylglycerides. In some embodiments, the bacterial cells do not express an exogenous xylose-metabolism gene. In some embodiments, the bacterial cells are spontaneous mutants. In some embodiments, the bacterial cells express at least one native, cryptic xylose-metabolism gene. In some embodiments, the bacterial cells produce triacylglycerides in the absence of an antibiotic. In some embodiments, the bacterial cells are, or are representative of, cells designated *Rhodococcus opacus* MITXM-61 (also referred to herein as "MITXM-61"), deposited with the ATCC® Patent Depository on Oct. 26, 2011, and having the deposit number PTA-12196. A "representative cell" is one that is derived from, obtained from, or produced from a cell designated *Rhodococcus opacus* MITXM-61, deposited with the ATCC® Patent Depository on Oct. 26, 2011, and having the deposit number PTA-12196. In some embodiments, a "representative cell" is a mutated or genetically engineered form of a cell designated *Rhodococcus opacus* MITXM-61, deposited with the ATCC® Patent Depository on Oct. 26, 2011, and having the deposit number PTA-12196.

In some embodiments, the culture medium comprises about 5 g/L to about 240 g/L xylose.

In some embodiments, triacylglycerides are produced in an amount of at least 14 g/L to 16 g/L of culture medium (or about 14 g/L to about 16 g/L). In some embodiments, the amount of triacylglycerides produced during stationary phase of growth of the population of bacterial cells is at least 40% (or about 40%) of the bacterial cell dry weight. In some embodiments, the amount of triacylglycerides produced during stationary phase of growth of the population of bacterial cells is at least 50% (or about 50%) of the bacterial cell dry weight. In some embodiments, the amount of triacylglycerides produced during stationary phase of growth of the population of bacterial cells is at least 60% (or about 60%) of the bacterial cell dry weight.

In some embodiments, the culture medium further comprises glucose. In some embodiments, the culture medium is not supplemented with a xylose metabolism enzyme. In some embodiments, the culture medium comprises xylose isolated from a lignocellulose biomass. In some embodiments, the culture medium does not comprise fermentation inhibitors. In some embodiments, the culture medium comprises xylose, $(NH_4)_2SO_4$, $MgSO_4 \cdot 7H_2O$, $CaCl_2 \cdot 2H_2O$, trace element solution, stock A solution, and phosphate buffer.

In some embodiments, the *Rhodococcus* cells are *Rhodococcus opacus* cells. In some embodiments, the *Rhodococcus opacus* cells are *Rhodococcus opacus* PD630 cells. In some embodiments, the bacterial cells are, or are representative of, cells designated *Rhodococcus opacus* MITXM-61, deposited with the ATCC® Patent Depository on Oct. 26, 2011, and having the deposit number PTA-12196.

In some embodiments, the methods may further comprise collecting the culture medium, collecting the triacylglycerides from the cell culture medium, or collecting both the cell culture medium and the triacylglycerides from the cell culture medium.

Also provided herein is culture medium produced by any one of the methods described herein.

In some aspects, provided herein are *Rhodococcus* bacterial cells that metabolize xylose, wherein the bacterial cells do not express an exogenous xylose-metabolism gene. In some embodiments, the bacterial cells are spontaneous mutants. In some embodiments, the bacterial cells express at least one native, cryptic xylose-metabolism gene. In some embodiments, the bacterial cells grow in the absence of an antibiotic. In some embodiments, the bacterial cells are *Rhodococcus opacus* (*R. opacus*) cells. In some embodiments, the bacterial cells are *R. opacus* PD630 cells. In some embodiments the bacterial cells are, or are representative of, cells designated *Rhodococcus opacus* MITXM-61, deposited with the ATCC® Patent Depository on Oct. 26, 2011, and having the deposit number PTA-12196.

In some aspects, provided herein are cell populations comprising any of the bacterial cells described herein, for example, bacterial cells that are, or are representative of, cells designated *Rhodococcus opacus* MITXM-61, deposited with the ATCC® Patent Depository on Oct. 26, 2011, and having the deposit number PTA-12196. In some embodiments, the cell population produces triacylglycerides in the presence of culture medium supplemented with xylose. In some embodiments, the cell population produces triacylglycerides in an amount of at least 14 g/L to 16 g/L of culture medium supplemented with about 5 g/L to about 240 g/L xylose. In some embodiments, during stationary phase of their cell growth, the cell population produces triacylglycerides in an amount that is at least 40%, at least 50% or at least 60% of the bacterial cell dry weight.

In some aspects, provided herein are methods comprising (a) combining alkalis (e.g., NaOH) with lignocellulose material, (b) heating, purifying, drying, and grinding the material to obtain a fibrous powder, (c) combining the fibrous powder with acids (e.g., HCl), hemicellulose, exoglucanase, endoglucanase and beta-glucosidase to form a suspension having a pH of about 3.0 to about 7.0, and (d) incubating the suspension at about 20° C. to 70° C. In some embodiments, sugar is released from the lignocellulose material in an amount of at least 75 grams (g) within 72 hours. In some embodiments, the lignocellulose material is corn stover silage. In some embodiments, the lignocellulose material is sorghum silage. In some embodiments, the lignocellulose material a combination of corn stover and sorghum silage.

In some embodiments, the cells (and cell populations) described herein, are cells designated *Rhodococcus opacus* MITXM-61, deposited with the ATCC® Patent Depository, 10801 University Boulevard, Manassas, VA 20110-2209, on Oct. 26, 2011, and having the deposit number PTA-12196. Also provided herein are derivatives or genetic/spontaneous mutants of any of the cell lines described herein.

BRIEF DESCRIPTION OF DRAWINGS

FIG. 4A: fatty acid content as a percent of cell dry weight (CDW). FIG. 4B: residual xylose and $(NH_4)_2SO_4$ present in the culture supernatants. FIG. 4C: fatty acid production kinetics and CDW.

FIG. 5A: fatty acid content as a percent of cell dry weight (CDW). FIG. 5B: residual xylose and $(NH_4)_2SO_4$ present in the culture supernatants. FIG. 5C: fatty acid production kinetics and CDW.

FIG. 6A: fatty acid content as a percent of cell dry weight (CDW). FIG. 6B: residual xylose, glucose, and $(NH_4)_2SO_4$ present in the culture supernatants. FIG. 6C: fatty acid production kinetics and CDW.

FIG. 10A: fatty acid content as a percent of cell dry weight (CDW). FIG. 10B: residual xylose, glucose and $(NH_4)_2 SO_4$ present in the culture supernatants. FIG. 10C: fatty acid production kinetics and CDW.

FIG. 12A: fatty acid content as a percent of cell dry weight (CDW). FIG. 12B: residual xylose, glucose and $(NH_4)_2 SO_4$ present in the culture supernatants. FIG. 12C: fatty acid production kinetics and CDW.

FIG. 14A: fatty acid content as a percent of cell dry weight (CDW). FIG. 14B: residual xylose, glucose and $(NH_4)_2 SO_4$ present in the culture supernatants. FIG. 14C: fatty acid production kinetics and CDW.

DETAILED DESCRIPTION OF INVENTION

Figure 1:
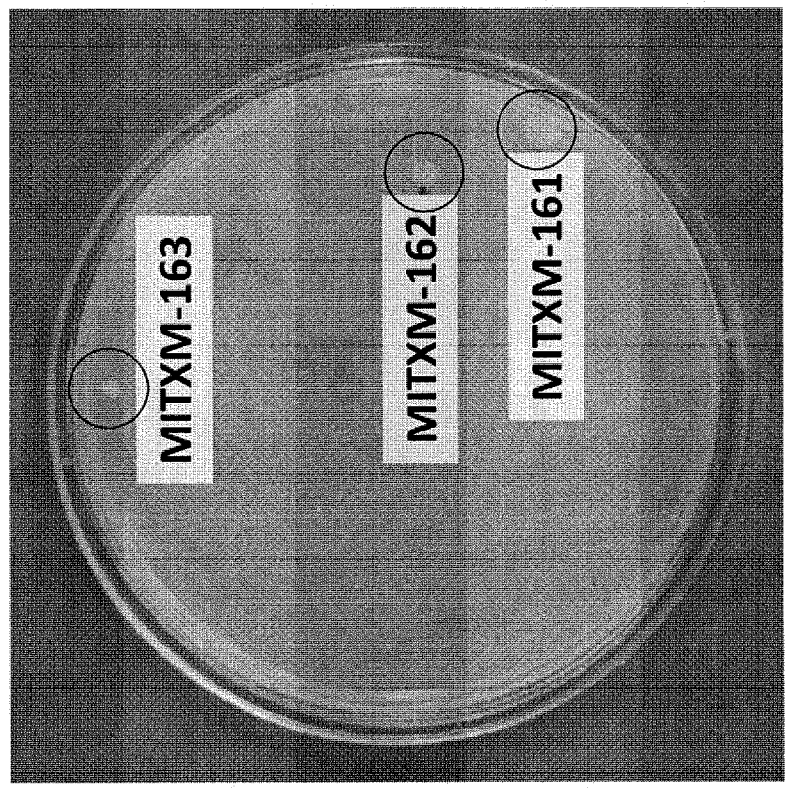
FIG. 1 shows a photograph of xylose-utilizing colonies of *R. opacus* on xylose-enriched agar plates.
Figure 1:
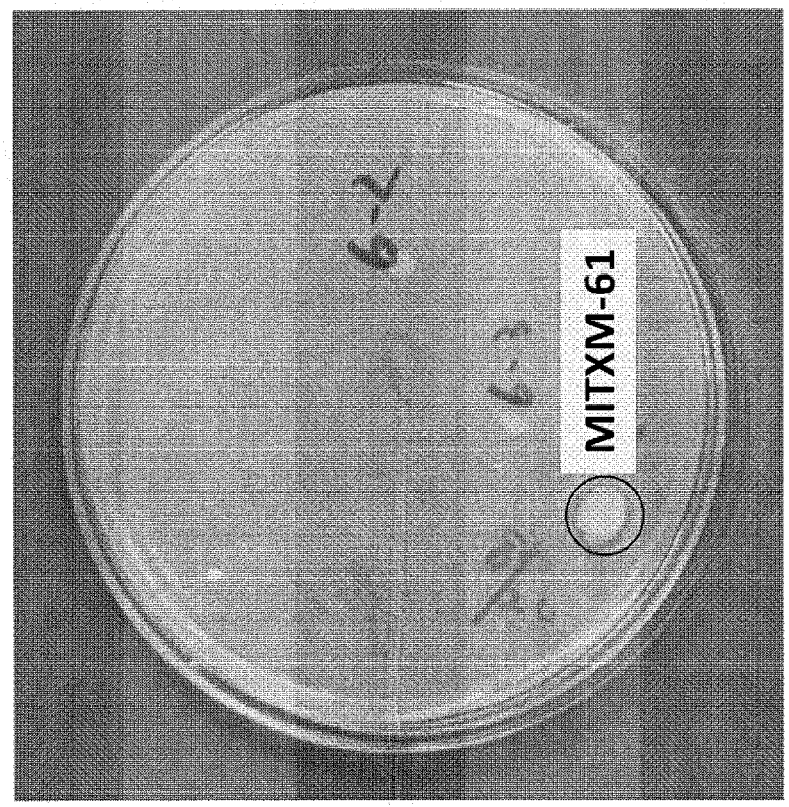

Aspects of the invention relate to methods for production of triacylglycerides (TAGs) in bacterial cells. Described herein are methods for high titer production of TAGs in xylose-containing medium. Also described herein are variant bacterial cells and methods of using such cells for production of TAGs in culture medium containing xylose, or xylose and glucose. These variant cells have activated spontaneously at least one native, cryptic gene involved in xylose metabolism, allowing for growth and TAG (triacylglyceride) production on xylose-containing medium, in some embodiments, without the addition of an antibiotic. Some aspects described herein relate to methods for production of TAGs in bacterial cells grown in the presence of a saccharified solution derived from renewable (e.g., non-food) biomass material. This saccharified solution includes xylose and glucose.

As used herein, "xylose" refers to the sugar xylose (e.g., the monosaccharide containing five carbon atoms and an aldehyde functional group), xylan (e.g., polysaccharides made from units of xylose), and other xylose polymers. Similarly, "glucose" refers to the simple sugar glucose, glucan, and other glucose polymers.

Some methods described herein relate to the production of TAGs. Triacylglycerides are also referred to as triacylglycerols or triglycerides. As used herein, a TAG refers to a glyceride in which the glycerol is esterified with three fatty acids. As used herein, a fatty acid refers to an organic acid made up of molecules containing a carboxyl group at the end of a hydrocarbon chain. The fatty acid components of the TAG can have chains of varying lengths. For example, in some embodiments the carbon content of the fatty acid may vary from 2 to 34 carbons. Several non-limiting examples of fatty acids include myristic acid, pentadecanoic acid, palmitic acid, palmitoleic acid, heptadecanoic acid, cis-10heptadecanoic acid, stearic acid, oleic acid, caproic acid, linoleic acid, linolenic acid, elcosenoic acid, behenic acid and erucic acid.

In some embodiments, the oleaginous microorganism used for TAG production is a species of *Rhodococcus* such as *Rhodococcus opacus*, for example *Rhodococcus opacus* PD630 (*R. opacus* PD630). In species of *Rhodococcus*, 10-80% of cell dry weight is fatty acid. The stored lipids that accumulate in *Rhodococcus* are mainly TAGs having a chain of 16 to 18 carbons (e.g., C16-C18.1 TAGs) that can be converted to biodiesel and other fuels. *R. opacus* PD630 undergoes a developmental process leading to abundant lipid storage involving increased lipid accumulation that can be detected by lipophilic dyes such as Nile Red, morphological changes from elongated rods to rotund cocci, and cell shortening as the cells develop under defined medium conditions. Shorter fragmented cells filled with lipid bodies can be separated using buoyant density separations.

*R. opacus* PD630 cells do not naturally utilize/ferment xylose. Existing genetically engineered *R. opacus* PD630 cells express exogenous xylose metabolism genes, but require the presence of an antibiotic for their growth. By contrast, the variant mutant *R. opacus* PD630 cells provided herein ferment high concentrations of xylose (e.g., ≥100 g/L) to produce high titers of TAGs (e.g., ≥10 g/L) and grow (or are capable of growing) in the absence of an antibiotic. In some embodiments, variant mutant cells provided herein are derived from (e.g., obtained from) or are spontaneous mutants of genetically engineered *R. opacus* PD630 cells. In some embodiments, the variant mutant cells in accordance with the invention do not express the same exogenous (genetically introduced) genes (e.g., xylA, xylB from *S. padanus*) as the parent strain.

In some embodiments, a population of *R. opacus* PD630 cells may be cultured for TAG production. A population of cells refers to more than one cell (e.g., at least two cells). In some embodiments, the population of cells comprises one strain of bacteria, while in other embodiments, the population of cells comprises more than one strain (e.g., two, three, four, five or more strains). For example, in some embodiments, the population of cells comprises a mutant variant *R. opacus* PD630 strain described herein as well as any of the strains described in WO 2010/147642, the entire teachings of which are incorporated herein by reference. In some embodiments, about 50% to 100% of the population of cells is of the mutant variant strain described herein. In some embodiments, greater than about 50, 55, 60, 65, 70, 75, 80, 85, 90, or 95% of the cell population is of mutant variant cells. In some embodiments, the cell population comprises greater than or equal to about 95% (or greater than or equal to 95%) mutant variant cells and less than or equal to about 5% (or greater than or equal to 5%) of non-variant mutant cells, such as wild-type *R. opacus* PD630 cells or genetically engineered (e.g., recombinant) *R. opacus* PD630 cells.

Mutant variant cells provided herein express at least one native, cryptic xylose metabolism gene. Cryptic genes are phenotypically silent DNA sequences, not normally expressed during the life cycle of an individual (e.g., microorganism). Xylose metabolism genes include xylose isomerases, xylose reductases, xylulose kinases, xylose dehydrogenases, xylitol dehydrogenases, xylonite dehydrogenases, xylonolactonases, aldehyde dehydrogenases, and xylose transporters. In some embodiments, the mutant variant cells are spontaneous mutants (rather than induced mutants). Spontaneous mutations can be caused by tautomerism (base change by the repositioning of a hydrogen atom, altering the hydrogen bonding pattern of that base resulting in incorrect base pairing during replication), depurination (loss of a purine base (A or G) to form an apurinic site (AP site)), deamination (hydrolysis changes a normal base to an atypical base containing a keto group in place of the original amine group), or slipped strand mispairing (denaturation of the new strand from the template during replication, followed by renaturation in a different spot). Spontaneous mutations can lead to activation of cryptic genes.

Some embodiments relate to the use of controlled growth conditions to maximize TAG production. Bacterial cells described herein can be cultured in medium of any type (nutrient or minimal) and any composition. The culture medium can be liquid (e.g., Lysogeny Broth (LB)) or gel/solid (e.g., LB mixed with agar and poured into Petri dishes). As would be understood by one of ordinary skill in the art, routine optimization would allow for use of a variety of types of medium. The selected medium can be supplemented with various additional components. Some non-limiting examples of supplemental components include antibiotics (e.g., amphotericin B, ampicillin, chloramphenicol, ciprofloxacin, gentamicin, hygromycin B, kanamycin, neomycin, penicillin, puromycin, streptomycin and tetracycline), isopropyl β-D-1-thiogalactopyranoside (IPTG) for gene induction, and ATCC® Trace Mineral Supplement. In some embodiments, TAGs are produced in the absence of supplements. An example of a defined medium for use as described herein is presented in Table I. In some embodiments, the *R. opacus* PD630 bacterial cells (e.g., mutant variants) described herein grow (or are capable of growing) and produce (or are capable of producing) TAGs in the absence of an antibiotic (e.g., gentamicin).

TABLE I

| | |
|---|---|
| Xylose | Varied from 0 to 240 g l$^{-1}$ |
| (NH$_4$)$_2$SO$_4$ | Varied from 0 to 15 g l$^{-1}$ |
| CaCl$_2$•2H$_2$O | 0.045 g l$^{-1}$ |
| 1M phosphate buffer (pH 7)* | 17.6 ml l$^{-1}$ |
| A9 trace elements solution* | 3.0 ml l$^{-1}$ |
| Stock A solution* | 3.0 ml l$^{-1}$ |

*Chartrain et al. *J. Ferment. Bioeng.* 86, 550-558 (1998), incorporated by reference.

Several non-limiting examples of growth conditions that affect fermentation include agitation speed, oxygen content, pH, temperature, glucose concentration, nitrogen concentration and the carbon to nitrogen (C/N) ratio. In some embodiments, the agitation speed of the culture may be about 50 to 1200 rpm. In some embodiments, the agitation speed may be more than 1200 rpm. For example, the agitation speed may be about 300, 400, 500, 600, 700, 800, 900, 1000, 1100, 1200 rpm, including any intermediate value. In some embodiments, the oxygen content of the culture may be above 80% with pure O$_2$. The pH of the culture may be about 4.0 to 9.0. For example, the pH may be about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9, including any intermediate value. In some embodiments, the pH is about 6.9 or 7.0. In some embodiments, the temperature of the culture may be about 20° C. to 45° C. For example, the temperature may be about 20, 21, 22, 23, 24, 25, 26, 27, 28, 29, 30, 31, 32, 33, 34, 35, 36, 37, 38, 39, 40, 41, 42, 43, 44 or 45° C., including any intermediate value. In some embodiments, the temperature is about 30° C.

The xylose concentration in the culture medium may be about 1 g/L to about 300 g/L. In some embodiments, the xylose concentration is about 5 g/L to about 240 g/L. For example, in some embodiments, the xylose concentration is about 40, 50, 60, 70, 80, 90, 100, 110, 120, 130, 140, 150, 160, 170, 180, 190, 200, 210, 220, 230, 240 or more than 240 g/L, including any intermediate value. In some embodiments, the culture medium may comprise both xylose and glucose. In some embodiments, the concentration of glucose may be about 1 g/L to about 300 g/L. In some embodiments, the glucose concentration may be about 40 g/L to about 240 g/L. For example, in some embodiments, the glucose concentration may be about 40, 50, 60, 70, 80, 90, 100, 110, 120, 130, 140, 150, 160, 170, 180, 190, 200, 210, 220, 230, 240 or more than 240 g/L, including any intermediate value. The sugars used for fermentation in the methods and compositions described herein may be refined or unrefined. In some embodiments, the sugars xylose, glucose or both (xylose and glucose) are comprise within a solution (e.g., saccharified solution) derived from a renewable biomass material such as, for example, corn stover silage or sorghum silage. As used herein, a saccharified (sugar) solution may be any solution comprising at least one sugar that has been converted from a biomass substrate. In some embodiments, a saccharified solution comprises a total sugar concentration of about 20 g/L to about 200 g/L. For example, in some embodiments, the total sugar concentration in the saccharified solution is about 40, 50, 60, 70, 80, 90, 100, 110, 120, 130, 140, 150, 160, 170, 180, 190, or 200 g/L. In some embodiments, the saccharified solution comprises a total sugar concentration of greater than 200 g/L. In some embodiments, a population of mutant variant cells that is cultured in greater than about 100 g/L saccharified solution accumulates greater than about 10 g/L TAGs. The sugar concentrations depend on, for example, the amount of starting material (substrate), the particular enzymes used to release the sugars from the biomass, the duration of the bioprocess required to release the sugars from the biomass, and any additional substrate that is added during the bioprocess, described below.

Several non-limiting factors that can be analyzed to evaluate TAG production in cell culture include xylose consumption, glucose consumption, cell dry weight and total fatty acid production. In some embodiments, these parameters are measured in grams per liter (g/L). In some embodiments, maximum production of fatty acids is achieved, in the presence of xylose, using a defined medium, containing about 120 g/L xylose. In some embodiments, maximum production of fatty acids is achieved, in the presence of xylose, using a defined medium, containing about 80 g/L glucose and about 40 g/L xylose. In some embodiments, maximum fatty acid production under these conditions is about 15 g/L, representing about 50% of the cell dry weight (CDW).

It should be appreciated that the lipids produced by the methods described herein may be purified by many different means. Control of medium and characterization of kinetics of storage lipid production and cell weakening allows for the production and harvesting of valuable stored lipids that may be used for the chemical conversion to Fatty Acid Methyl Esters (FAMEs), routinely used as biodiesel fuel.

Some aspects of the invention relate to the generation of bacterial cells that can metabolize xylose and the use of such bacterial cells in TAG production. As presented in Example 1, previously engineered transformant *R. opacus* PD630 cells containing exogenous xylose-metabolizing genes xylA and xylB from *Streptomyces padanus* (*S. padanus*) (see WO 2010/147642), when grown on xylose-containing medium in the absence of an antibiotic, led to the production of mutant variant bacterial species. These mutant variants metabolize xylose and produce high yields of TAGs in the presence of xylose-containing medium, but no longer express the exogenous xylose-metabolism gene xylA from *S. padanus*.

In some aspects of the invention, high titers of TAGs are produced through culturing oleaginous bacterial cells. As used herein, "high titer" refers to a titer in the grams per liter (g/L) scale. The titer produced for a given TAG will be influenced by multiple factors including choice of medium. In some embodiments, the titer for production of total fatty acids is at least 1 g/L. For example the titer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 g/L, including any intermediate values. In some embodiments, the titer is about 12 g/L, while in other embodiments, the titer is about 15 g/L or about 16 g/L.

In some embodiments, the variant mutant cells are cultured until they reach stationary phase of bacterial cell growth. Bacterial growth in batch culture can be modeled with four different phases: lag phase (A), exponential or log phase (B), stationary phase (C), and death phase (D). During lag phase, bacteria adapt to growth conditions. It is the period where the individual bacteria are maturing and not yet able to divide. During the lag phase of the bacterial growth cycle, synthesis of RNA, enzymes and other molecules occurs. In this phase, the microorganisms are not dormant. Exponential phase (sometimes called the log phase or the logarithmic phase) is a period characterized by cell doubling. The number of new bacteria appearing per unit time is proportional to the present population. If growth is not limited, doubling will continue at a constant rate so that the number of cells, and the rate of population increase, doubles with each consecutive time period. For this type of exponential growth, plotting the natural logarithm of cell number against time produces a straight line. The slope of this line is the specific growth rate of the organism, which is a measure of the number of divisions per cell per unit time. The actual rate of this growth depends upon the growth conditions, which affect the frequency of cell division events and the probability of both daughter cells surviving. Exponential growth cannot continue indefinitely, however, because the medium is soon depleted of nutrients and enriched with wastes. During stationary phase, the growth rate slows as a result of nutrient (e.g., xylose) depletion and accumulation of toxic products. This phase is reached as the bacteria begin to exhaust the resources that are available to them. This phase is a constant value as the rate of bacterial growth is equal to the rate of bacterial death. At death phase, bacteria run out of nutrients and die. As demonstrated in the Examples section, growth of the mutant variant *R. opacus* PD630 cells described herein in batch-culture, including about 12% xylose (or ~12% xylose and glucose), can reach, at stationary phase, a cell density of about 20-35 g/L CDW with a fatty acid content of about 40-60% of the CDW, accounting for about 10-20 g/L of fatty acids. In some embodiments, stationary phase is reached concomitant with complete (or near complete) consumption of xylose (or xylose and glucose) in the medium.

The liquid cultures used to grow cells associated with the invention can be housed in any of the culture vessels known and used in the art. In some embodiments, large scale production in an aerated reaction vessel such as a stirred tank reactor can be used to produce large quantities of the TAGs associated with the invention. It should be appreciated that any means of purification of TAGs from cell culture medium is compatible with the invention.

Aspects of the invention include strategies to optimize triacylglyceride (TAG) production from a cell. Optimized production of a TAG refers to producing a higher amount of a TAG following pursuit of an optimization strategy than would be achieved in the absence of such a strategy.

In some embodiments, it may be advantageous to use a cell that has been optimized for production of at least one TAG. For example, it may be optimal to further mutate the mutant variant cells described herein prior to growing the cells for TAG production. In some embodiments, screening for additional mutations that lead to enhanced production of at least one TAG may be conducted through a random mutagenesis screen, or through screening of known mutations. In some embodiments, shotgun cloning of genomic fragments may be used to identify genomic regions that lead to an increase in production of at least one TAG, through screening cells or organisms that have these fragments for increased production of at least one TAG. In some cases, at least one mutation may be combined in the same cell or organism.

Some aspects of the invention are directed to biofuel or TAG fermentation from renewable biomass material. Xylose and glucose (and other simple sugars) can be derived from such material. Examples of renewable biomass materials for use with the aspects and embodiments described herein include renewable lignocellulose biomass material (e.g., non-food polysaccharides such as, for example, corn stover silage and sorghum silage). In plant cell walls, cellulose and hemicellulose are covered with lignin, a phenolic polymer that hinders the degradation of cell wall polysaccharides to simple sugars, which can be fermented into biofuels (e.g., TAGs). Pretreatment of lignocellulose biomass material permits efficient conversion of polysaccharides to simple sugars, however, small concentrations of by-products from such pretreatments, including phenols, furans and organic acids, can hinder oil production/fermentation by oleaginous microorganisms. Provided herein are methods of biological conversion of renewable biomass material to simple sugars, and subsequently to biofuel, in the absence of fermentation inhibiting by-products.

The Examples which follow are illustrative of specific embodiments of the invention, and various uses thereof. They are set forth for explanatory purposes only, and are not to limit the invention.

EXAMPLES

Strain and Medium

Bacterial strain R. opacus PD630 (DSM 44193) was obtained from Deutsche Sammlung von Mikroorganismen and Zellkulturen GmbH (DSMZ, Germany). All variants were constructed in the laboratory. A combination of Lysogeny broth (LB) (Beltane, J. Bacterial., 62, 293-300 (1951)) and a xylose-defined medium was used as the defined culture medium (defined medium), which contained per liter: 16.0 g xylose, 1.0 g $(NH_4)_2SO_4$, 1.0 g $MgSO_4.7H_2O$, 0.015 g $CaCl_2.2H_2O$, 1.0 ml trace element solution, 1.0 ml stock A solution and 35.2 ml 1.0 M phosphate buffer. The trace element solution, stock A solution, and phosphate buffer were the same as those described by Chartrain et al. (J. Ferment. Bioeng. 86: 550-558, 1998), incorporated herein by reference. Xylose, $MgSO_4.7H_2O$, and $CaCl_2.2H_2O$ were dissolved in deionized water and sterilized by autoclaving, then the stock A solution, the trace element solution, and $(NH_4)_2SO_4$ were added to the cooled medium as filter sterilized stock solutions. Modifications to the defined medium for triacylglyceride production are described below. The bacterial strains were routinely maintained on 2% w/v LB agar medium at 4° C. and preserved in 20% v/v glycerol at −80° C.

Analytical Procedures

Cell growth was estimated by measuring optical density at 660 nm or by measuring the cell dry weight (CDW). The CDW was determined after lyophilizing culture biomass by centrifuging about 10 ml of culture broth at 6,500 rpm for 15 min and washing the cell pellet twice in deionized water. The lyophilized cell pellet was also used to analyze the fatty acid concentrations. The supernatants of the culture broth were used for analyses of residual glucose and $(NH_4)_2SO_4$ after filtration through a 0.2 µm pore-size filter. The residual glucose concentrations were measured by high-performance liquid chromatography (HPLC, Agilent 1100 system) fitted with an Aminex HPX-87H column (300×7.8 mm, BIO-RAD) coupled to a refractive index (RI) detector. The column was eluted with 5 millimolar (mM) $H_2SO_4$ as mobile phase at 40° C. and a flow rate of 0.6 ml/min. Residual ammonia concentrations were determined by the Ammonia Assay Kit (Sigma-Aldrich, St. Louis, Mo.) according to the manufacturer's instructions. To determine the fatty acid content of the cells and the composition of lipids, fatty acids were converted to methyl esters by methanolysis followed by gas chromatography (GC) (Brandl et al., Appl. Environ. Microbiol., 54, 1977-1982 (1988); Wältermann et al., Microbiology, 146, 1143-1149 (2000)). An average of 10.0 mg of lyophilized cells, or the triacylglyceride fraction obtained from preparative TLC, was resuspended in 1.0 ml of methanol containing 15% (v/v) $H_2SO_4$ and 1.0 ml of chloroform. Methanolysis was carried out at 100° C. for 2.5 h. After cooling to room temperature and then on ice, 0.5 ml of deionized water was added to the solution, which was then vortexed for 1 min. The organic phase containing fatty acid methyl esters (FAMEs) was analyzed by using an Agilent 6850 series II GC system equipped with an Agilent DB-Wax column (30.0 mm by 0.32 mm, 0.5 µm thick film) with hydrogen as the carrier gas. A 2 µl portion of the organic phase was injected with a 30:1 split ratio using the autosampler. The inlet was maintained at 250° C. The oven was held at 80° C. for 5 min, heated to 220° C. at 20° C./min, and then held at 220° C. for 5 min. Peak detection was performed by a flame ionization detector, which was maintained at 300° C. The fatty acids were identified and quantified by comparison to standard FAMEs (Sigma-Aldrich, St. Louis, Mo.). Fatty acid content was defined as the percentage of the ratio of fatty acids to cell dry weight (% CDW).

Chemicals

All chemicals used were reagent-grade and obtained from Sigma-Aldrich (St. Louis, Mo.), unless otherwise noted. All medium components were purchased from BD Diagnostic Systems (Difco, Sparks, Md.).

Example 1

Spontaneous Mutants of a Xylose Fermenting R. Opacus Strain

Figure 2:
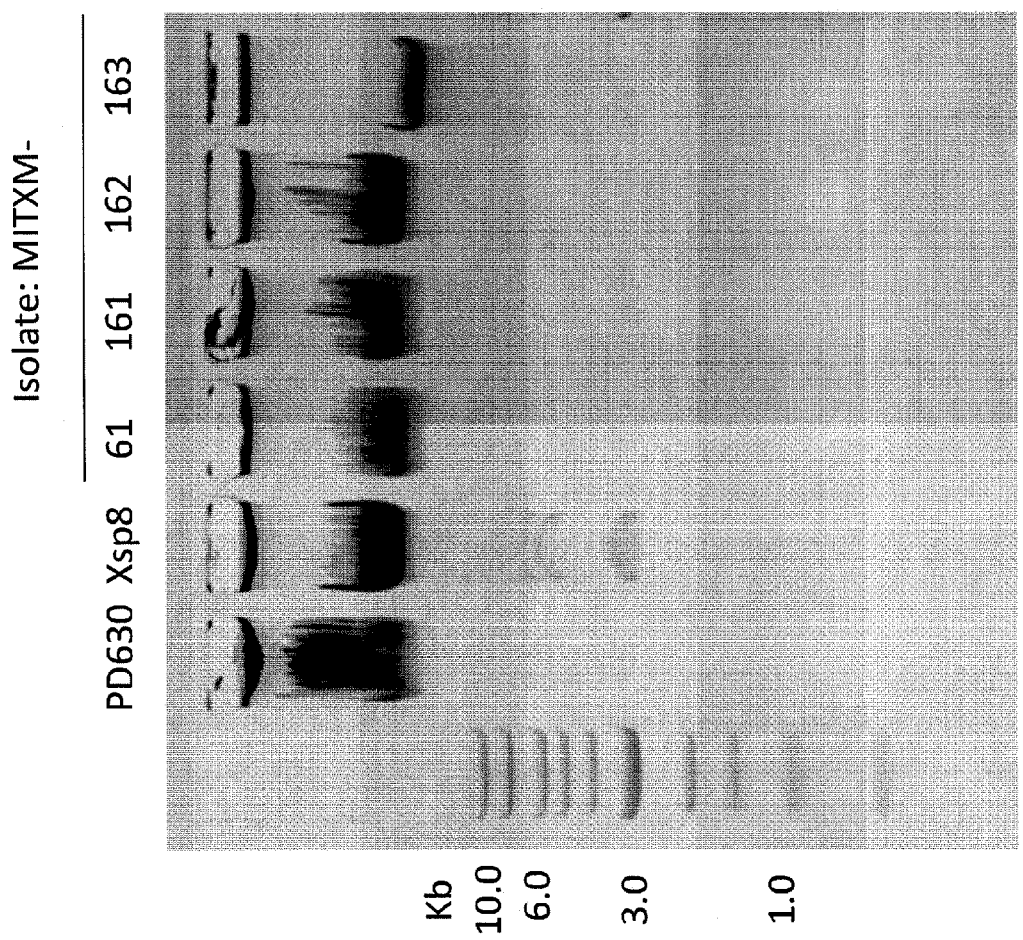
FIG. 2 shows an electrophoresis image of the genomic DNA of PD630 (lane 2), Xsp8 (lane 3), and four bacterial colony isolates, MITXM-61 (lane 4), MITXM-161 (lane 5), MITXM-162 (lane 6) and MITXM-163 (lane 7) on a 0.6% agarose gel. A 3603 base pair (bp) band representing a pAL358 plasmid, from the Xsp8 strain, harboring the genes xylA and xylB is visible in lane 3. Molecular weight markers are shown in lane 1.

The plasmid-cured strain from a transformant (Xsp8) of R. opacus PD630, which carried xylA and xylB on a plasmid, was prepared (see WO 2010/147642), and the cells were spread on a defined agar medium with 16.0 g/L xylose and 1.0 g/L $(NH_4)_2SO_4$. After 14 days of cultivation at 30° C., several colonies appeared on the plates (FIG. 1) and the colonies were isolated. The total cellular DNA of the original PD630 strain, the Xsp8 strain, and four new strains (MITXM-61, MITXM-161, MITXM-162 and MITXM-163) were analyzed by conventional agarose gel electrophoresis (FIG. 2). A plasmid was observed only in strain Xsp8, which contained a 3603 base pair (bp) DNA insert harboring the genes xylA and xylB in the pAL358 backbone.

Figure 3:
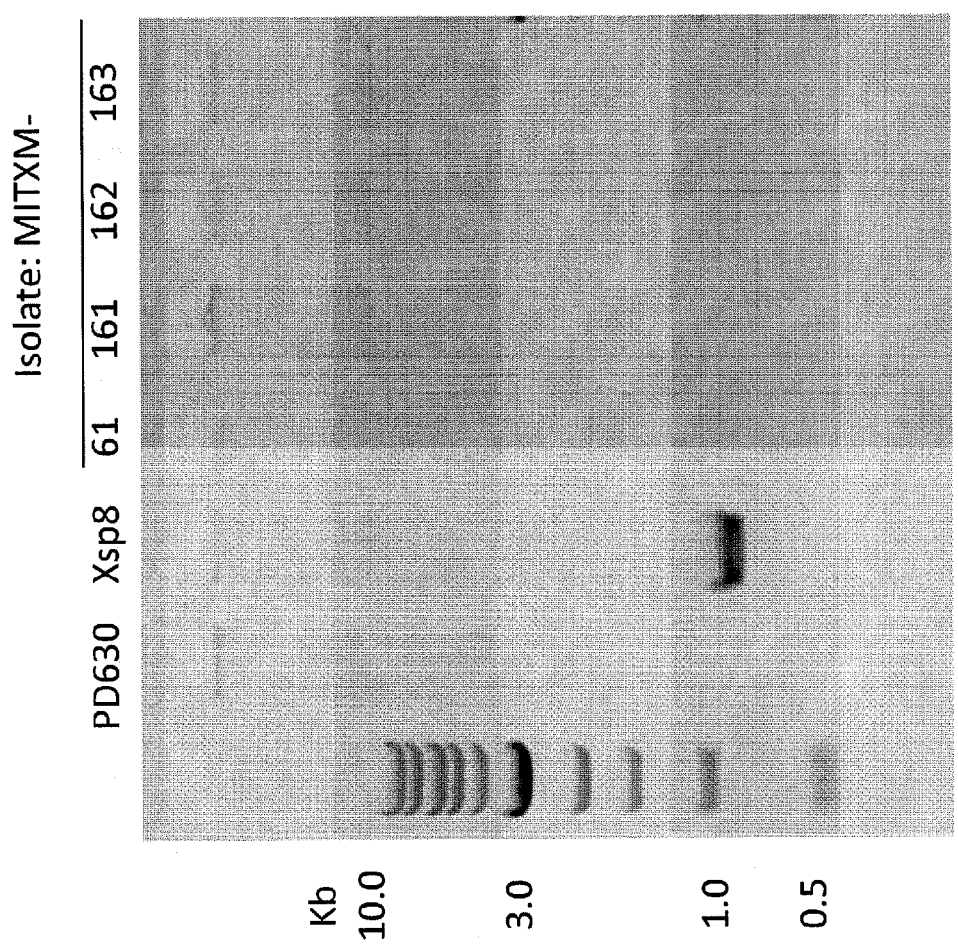
FIG. 3 shows an electrophoresis image of polymerase chain reaction (PCR)-amplified DNA from PD630 (lane 2), Xsp8 (lane 3), and four bacterial colony isolates, MITXM-61 (lane 4), MITXM-161 (lane 5), MITXM-162 (lane 6) and MITXM-163 (lane 7) on a 1% agarose gel. The DNA was amplified using a primer set (designated 3603-664f and 3603-1524r) derived from xylA of *S. padanus*. A 861 bp band from the Xsp8 strain is visible in lane 3. Molecular weight markers are shown in lane 1.

PCR amplification of genomic DNA for the original PD630 strain, the Xsp8 strain, and the four new isolated strains was carried out using a primer set (3603-664 forward and 3603-1524 reverse) derived from xylA of S. padanus. While no PCR products were obtained from genomic DNA of PD630 or of the four new strains, the PCR product amplified from genomic DNA of the Xsp8 strain was of the expected size (861 bp) (FIG. 3). These data demonstrate that the MITXM-61, MITXM-161, MITXM-162 and MITXM-163 strains are spontaneous mutants with cryptic xylose-metabolism genes activated and expressed in R. opacus (herein after referred to as "mutant variant" strains). These four mutant variant strains are different from that of the Xsp8 strain in that the Xsp8 strain expresses the heterologous genes encoding xylose isomerase (e.g., xylA) and/or the inserted gene encoding xylulose kinase.

Example 2

Lipid Production by Spontaneous Mutants in the Presence of Xylose

The potential of the four mutant variant strains to produce lipids (fatty acids) from xylose was examined. Table II presents a summary of lipid production of the four mutant variant strains and the Xsp8 strain in the presence of xylose. The mutant variant strains were used to inoculate 50 ml of defined medium containing 16 g/L xylose as the sole carbon source, with 1.0 g/L $(NH_4)_2SO_4$. The inoculated cultures were incubated on a rotary shaker (200 rpm) at 30° C. for 5 days. Xsp8 cells were grown in the presence of 10 mg/L gentamicin to ensure plasmid stability. All of the strains were able to metabolize xylose and grow. MITXM-61 and MITXM-161 accumulated 2.2 g/L of total fatty acid, over 40% of the cell dry weight (CDW) as fatty acids.

TABLE II

Lipid production of R. opacus spontaneous mutants on xylose.

| Strain | Growth CDW, g/L | Fatty acid production % CDW | g/L |
|---|---|---|---|
| MITXM-61 | 5.4 | 41 | 2.2 |
| MITXM-161 | 5.2 | 42 | 2.2 |
| MITXM-162 | 4.8 | 39 | 1.9 |
| MITXM-163 | 4.7 | 8 | 0.4 |
| Xsp8 | 5.2 | 39 | 2.0 |

Example 3

Time-Course Analysis of Lipid Production by MITXM-61 in the Presence of Xylose

Lipid production by the MITXM-61 strain grown in xylose-enriched defined medium in batch fermentors was investigated. MITXM-61 cells were first grown on a LB agar plate at 30° C. for 3 days. A loopful of the cells was inoculated into 100 ml of defined medium supplemented with 16 g/L xylose and 1.0 g/L $(NH_4)_2SO_4$ in a 500 ml baffled flask. The culture was incubated on a rotary shaker (200 rpm) at 30° C. for 3 days, and the cell density was adjusted to an $OD_{660}$ of 20. A 15 ml aliquot of the broth containing cells was transferred into a 500 ml fermentor vessel containing 300 ml working volume of modified defined medium: 120 g/L xylose, 7.5 g/L $(NH_4)_2SO_4$, 3.0 g/L $MgSO_4.7H_2O$, 0.045 g/L $CaCl_2.2H_2O$, 3.0 ml/L trace element solution, 3.0 ml/L stock A solution, and 17.6 ml/L 1.0 M phosphate buffer. A SIXFORS® bioreactor system (Infors AG CH-4103, Bottmingen, Switzerland) at an operating temperature of 30° C. was used. Dissolved oxygen was measured with an Ingold polarographic probe and was maintained at above 60% $O_2$ saturation by adjusting the agitation speed up to 1000 rpm and by automatically adjusting the mixture of air and pure oxygen flow via flow controllers while maintaining air gas flow at 1.0 VVM. When necessary to prevent foam formation, polypropylene glycol P 2000 (Fluka) was manually added to the fermentor vessel. The pH value in the medium was maintained at 6.9±0.1 by the addition of 2 M NaOH.

Figure 4:
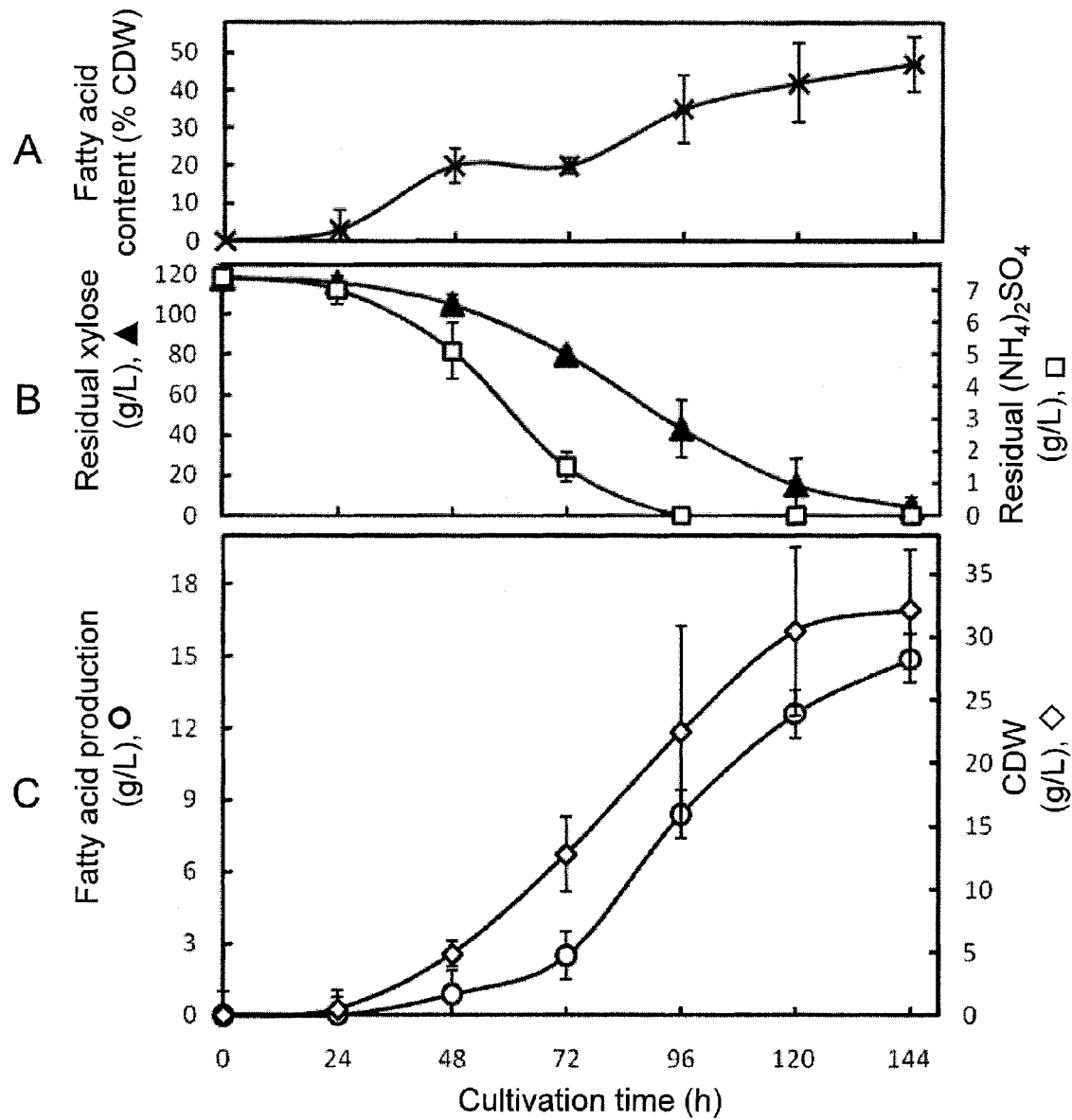
FIGS. 4A-4C show graphs depicting lipid production in *Rhodococcus opacus* bacterial strain MITXM-61 on substrate containing 120 g/L xylose, in a bioreactor, as a function of time.

The cell growth increased after 24 hours (h) of cultivation, and maximum fatty acid accumulation of 14.9 (±0.2) g/L, representing 47 (±7.2) %, of CDW, was obtained during stationary phase (144 hours post-inoculation), concomitant with the complete consumption of the xylose in the medium (FIGS. 4A-4C).

Example 4

Time-Course Analysis of Lipid Production by MITXM-61 in the Presence of Xylose

Figure 5:
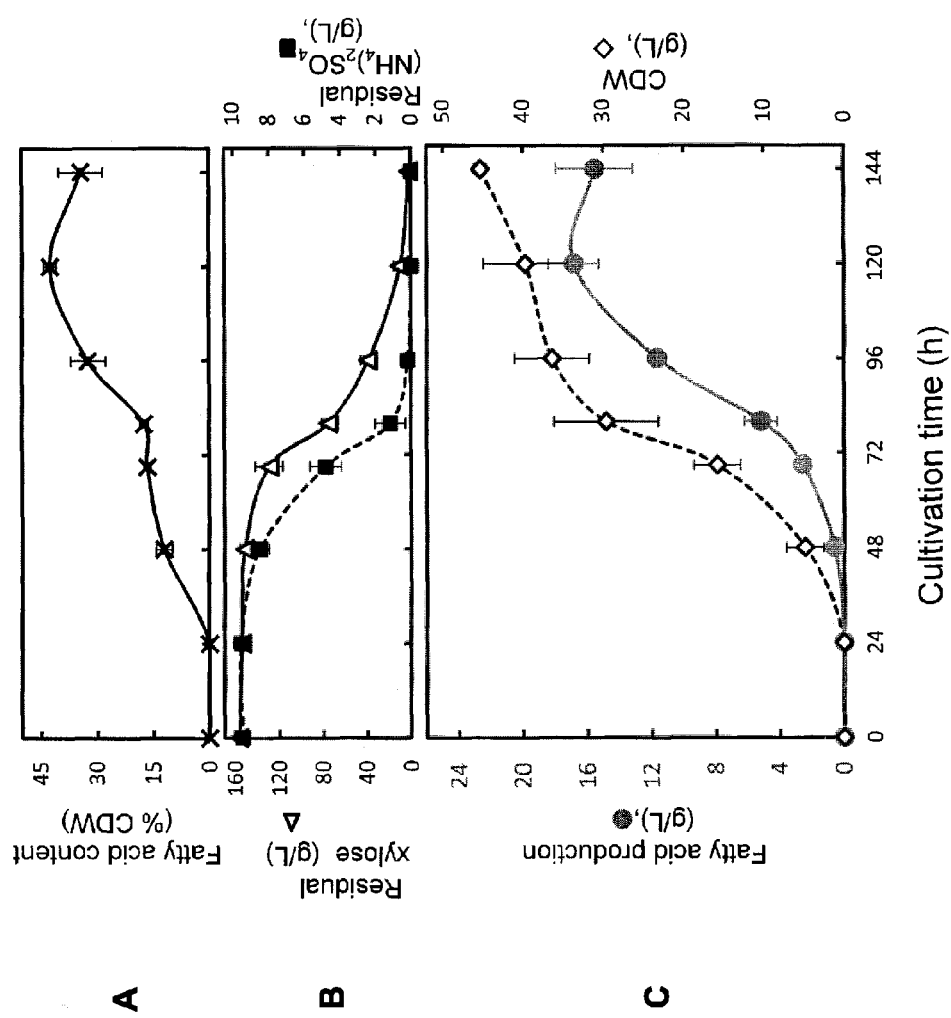
FIGS. 5A-5C show graphs depicting lipid production in *Rhodococcus opacus* bacterial strain MITXM-61 on substrate containing 159 g/L xylose, in a bioreactor, as a function of time.

FIG. 5 shows the time course of lipid production by MITXM-61 on xylose in a defined medium containing 159 g/L xylose and 9.63 g/L ammonium sulfate. Fatty acid production kinetics, CDW (cell dried weight), fatty acid content as percent of CDW, and residual xylose and ammonium sulfate present in the culture supernatant are shown in the figure. Lipid accumulation began when ammonium sulfate was almost fully consumed. After 120 h of cultivation, the maximum fatty acid accumulation was 16.9 g/L (43% CDW)—a productivity of 3.38 g/L/day, and the xylose in the medium was almost consumed.

Example 5

Time-Course Analysis of Lipid Production by MITXM-61 in the Presence of Xylose and Glucose Lipid production by the MITXM-61 strain grown in xylose- and glucose-enriched defined medium in batch fermentors was investigated. MITXM-61 cells were first grown on a LB agar plate at 30° C. for 3 days. A loopful of the cells was inoculated into 100 ml of defined medium supplemented with 12.0 g/L glucose, 6.0 g/L xylose, and 1.1 g/L $(NH_4)_2SO_4$ in a 500 ml baffled flask. The culture was incubated on a rotary shaker (200 rpm) at 30° C. for 2 days, and the cell density was $OD_{660}=18$. A 6.0 mL aliquot of the broth containing cells was transferred into 500 ml fermentor vessels containing 300 ml working volume of modified defined medium: 80 g/L glucose, 40 g/L xylose, 7.06 g/L $(NH_4)_2SO_4$, 3.0 g/L $MgSO_4.7H_2O$, 0.045 g/L $CaCl_2.2H_2O$, 3.0 ml/L trace element solution, 3.0 ml/L stock A solution, and 17.6 ml/L 1.0 M phosphate buffer. A SIXFORS® bioreactor system (Infors AG CH-4103, Bottmingen, Switzerland) at an operating temperature of 30° C. was used. Dissolved oxygen was measured with an Ingold polarographic probe and was maintained at above 60% $O_2$ saturation by adjusting the agitation speed up to 1000 rpm and by automatically adjusting the mixture of air and pure oxygen flow via flow controllers, while maintaining air gas flow at 1.0 VVM. When necessary to prevent foam formation, polypropylene glycol P 2000 (Fluka) was manually added to the fermentor vessel. The pH value in the medium was maintained at 6.9±0.1 by the addition of 2M NaOH.

After 72 hours of cultivation, 20 ml of the broth containing cells was transferred into a 2 L fermentor vessel filled with 1 L working volume of the modified defined medium: 80 g/L glucose, 40 g/L xylose, 7.06 g/L $(NH_4)_2SO_4$, 3.0 g/L $MgSO_4.7H_2O$, 0.045 g/L $CaCl_2.2H_2O$, 3.0 ml/L trace element solution, 3.0 ml/L stock A solution, and 17.6 ml/L 1 M phosphate buffer. The fermentation was performed using a BIOENGINEERING bioreactor system (R'ALF, Wald, Switzerland) at 30° C. The pH value in the medium was maintained at 6.9±0.1 by the addition of 2 M NaOH. Dissolved oxygen was measured with an Ingold polarographic probe and maintained at above 60% $O_2$ saturation by adjusting the agitation speed up to 1000 rpm, and by automatically adjusting the mixture of air and pure oxygen flow via flow controllers while maintaining air gas flow at 1.0 VVM.

Figure 6:
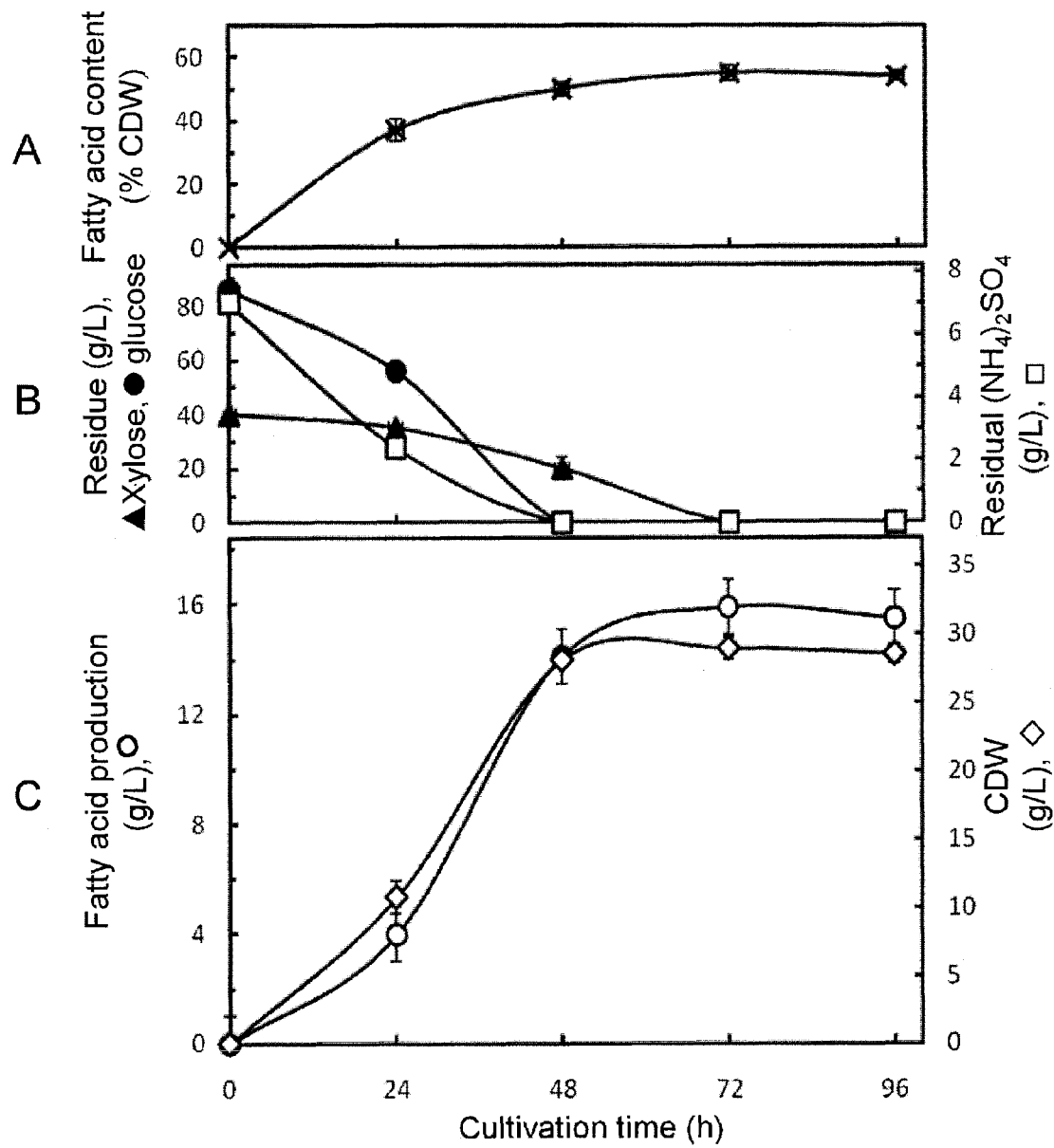
FIGS. 6A-6C show graphs depicting lipid production in *Rhodococcus opacus* bacterial strain MITXM-61 using a mixed-substrate of 40 g/L xylose and 80 g/L glucose, in a bioreactor, as a function of time.

The cell growth increased after 8 h of cultivation. The maximum fatty acid production was 15.9 (±1.2) g/L (55±2.3% CDW) after 72 h of cultivation, concomitant with the complete consumption of xylose and glucose in the medium (FIGS. 6A-6C).

Example 6

Preparation of a High Concentration Saccharified Corn Stover Solution

Figure 7:
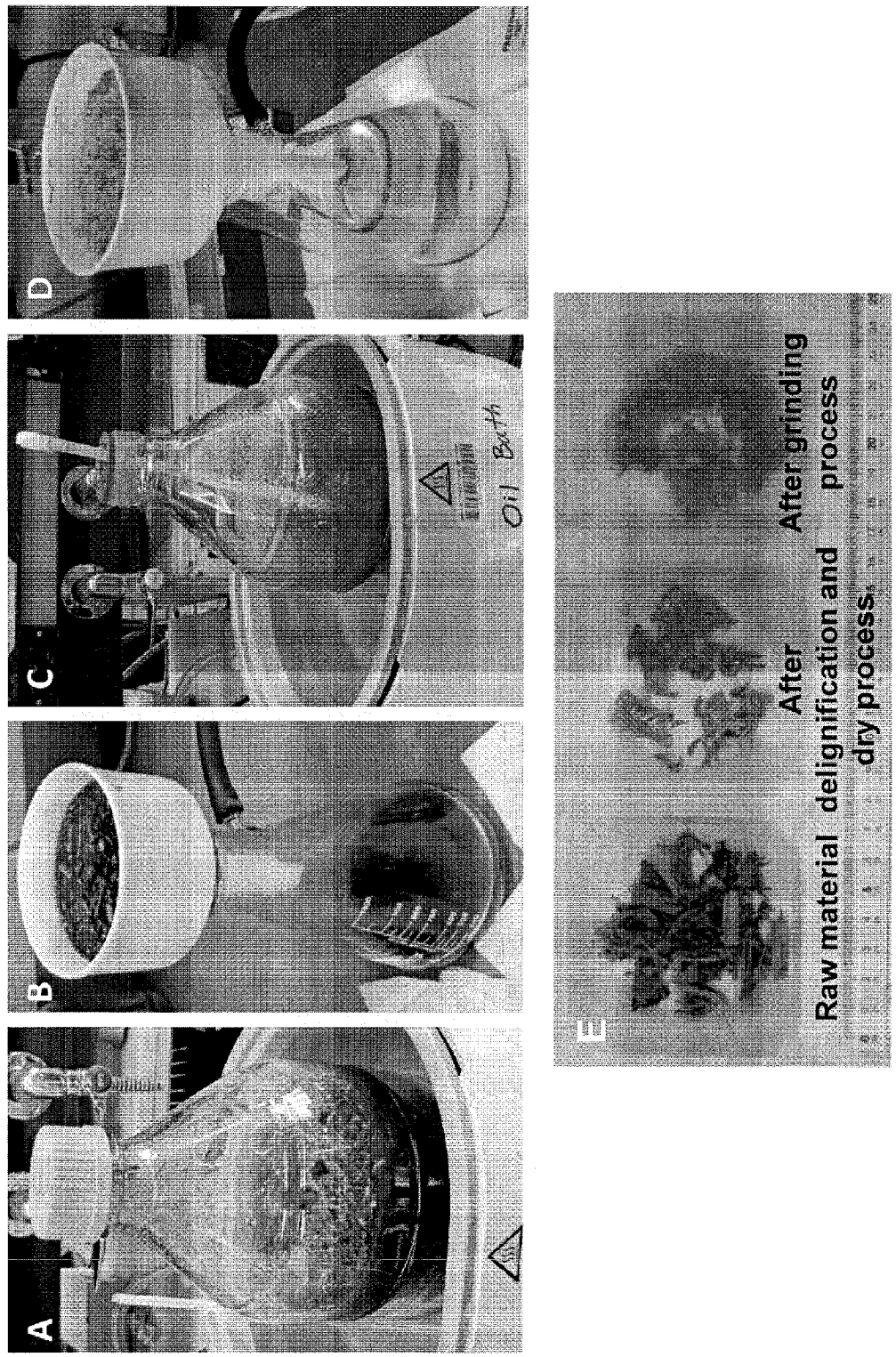
FIGS. 7A-7E depict images of a detoxification process for removing fermentation inhibitors from a renewable biomass.
Figure 8:
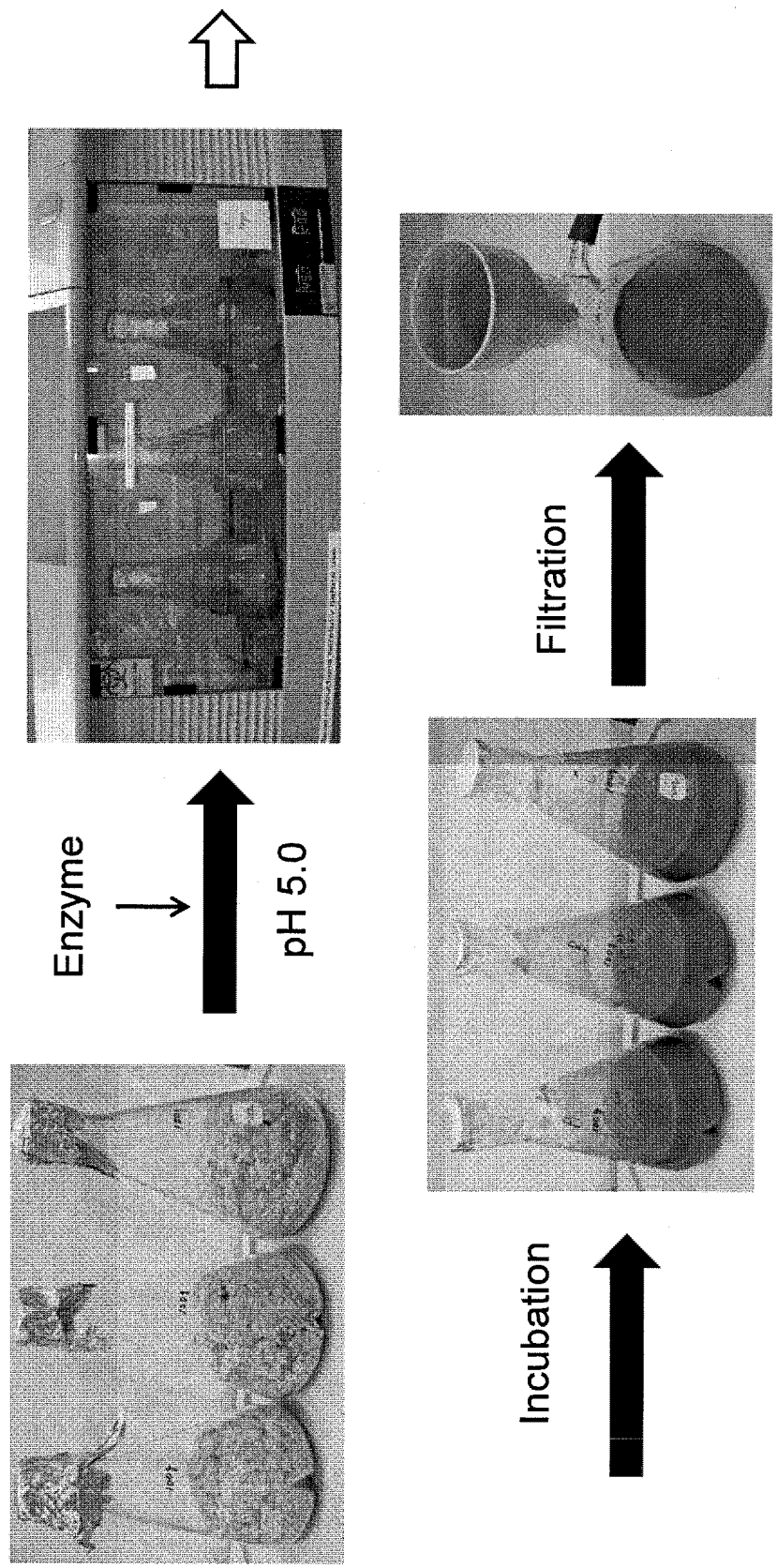
FIG. 8 depicts images of a process for saccharification of the detoxified renewable biomass.

Lignocellulosic biomass in the form of corn stover silage was the substrate in Examples 7-10. One hundred grams of corn stover silage (30 grams dry basis) was suspended in 500 ml of 1% (w/w) NaOH and heated at 90° C. (FIG. 7A). After 45 minutes (min) of incubation, the material was filtered (FIG. 7B), resuspended in 500 ml of a fresh 1% NaOH solution, and kept at 90° C. for 45 min (FIG. 7C). The slurry was filtered, and the residue was washed three times with 500 ml of water (FIG. 7D).

Figure 9:
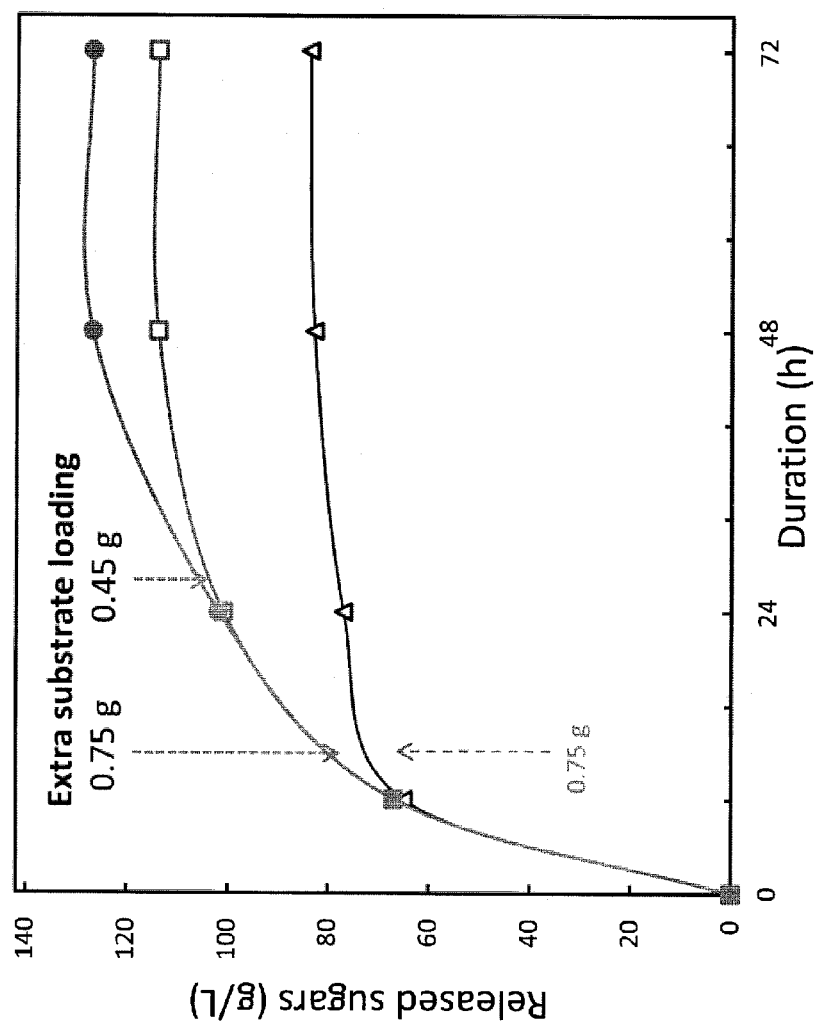
FIG. 9 shows a graph depicting enzymatic saccharification of pretreated corn stover silage as a function of time.

The pre-treated material was dried at 60° C. overnight in an oven and ground into fine particles using a grinder. Sixteen grams of the pretreated material were obtained as a fibrous powder. The pretreated corn silage (1.5 g) was suspended in 12.6 ml of 0.002 N HCl, and 0.75 ml of OPTIMASH® XL (GENENCOR®, Danisco US, Inc.) and 0.15 ml of ACCELLERASE® 1500 (GENENCOR®, Danisco US, Inc.) were added to the suspension. The suspension was adjusted to pH 5.0 with 0.1N HCl. The reaction was carried out at 200 rpm and 45° C. Additionally, pretreated materials were added as a single bolus dose (0.75 g after 8 h) or as a double bolus dose (0.75 g and 0.45 g respectively after 8 h and 24 h). The released sugars from the no bolus, the single bolus and the double bolus doses after 72 h of saccharification were 84 g/L, 114 g/L, and 127 g/L, respectively, of total single sugars (FIG. 9).

Example 7

Triacylglyceride Production by MITXM-61 Grown in Saccharified Corn Stover Solution Five hundred grams of corn stover silage (150 g dry basis) was suspended in 2.5 liters of 1% (w/w) NaOH and heated at 90° C. After 45 min of incubation, the material was filtered, resuspended in 2.5 liters of a fresh 1% NaOH, and kept at 90° C. for 45 min. To filter the material, the residue was washed three times with 2.5 liters of water. The washed material was dried at 60° C. overnight in an oven and ground into fine particles by a grinder to obtain 77 g of the pretreated material. The pretreated material (30 g) was suspended in 272 ml of 0.002 N HCl, and 15 ml of OPTIMASH® XL (GENENCOR®, Danisco US, Inc.) with 3 ml of ACCELLERASE® 1500 (GENENCOR®, Danisco US, Inc.) added to the suspension. The suspension was adjusted to pH 5.0 with 0.1N HCl. The reaction was carried out at 200 rpm and 45° C. Additionally, pretreated materials were added as a double bolus dose (15 g and 9 g respectively after 8 h and 24 h). The saccharified solution after 72 h of incubation contained 132 g/L of total sugars, including 90 g/L glucose, 37 g/L xylose, and 5 g/L of other sugars, and was used for fermentation of MITXM-61. MITXM-61 cultivation was performed using a SIXFORS® bioreactor system (Infors AG CH-4103, Bottmingen, Switzerland) at 30° C. A loopful of MITXM-61 cells grown on a LB agar plate at 30° C. for 3 days was inoculated into 100 ml of defined medium: 12 g/L glucose, 6 g/L xylose, and 1.1 g/L $(NH_4)_2SO_4$ in a 500 ml baffled flask. The culture was incubated on a rotary shaker (200 rpm) at 30° C. for 2 days and the cell density was 15.2 of $OD_{660}$. A 20 ml aliquot of the broth containing cells was transferred into a 500 ml fermentor vessel containing 180 ml of the saccharified corn stover solution and 20 ml of supplement solution consisting of 1.1 g $(NH_4)_2SO_4$, 0.6 g $MgSO_4.7H_2O$, 0.009 g $CaCl_2.2H_2O$, 0.6 ml trace element solution, 0.6 ml stock A solution, and 3.52 ml 1 M phosphate buffer. The pH value in the medium was maintained at 6.9±0.1 by the addition of 2 M NaOH. Dissolved oxygen was measured with an Ingold polarographic probe and maintained at above 60% $O_2$ saturation by adjusting the agitation speed up to 1000 rpm, and by automatically adjusting the mixture of air and pure oxygen flow via flow controllers while maintaining air gas flow at 0.1 VVM. When necessary to prevent foam formation, polypropylene glycol P 2000 (Fluka) was manually added to each vessel.

Figure 10:
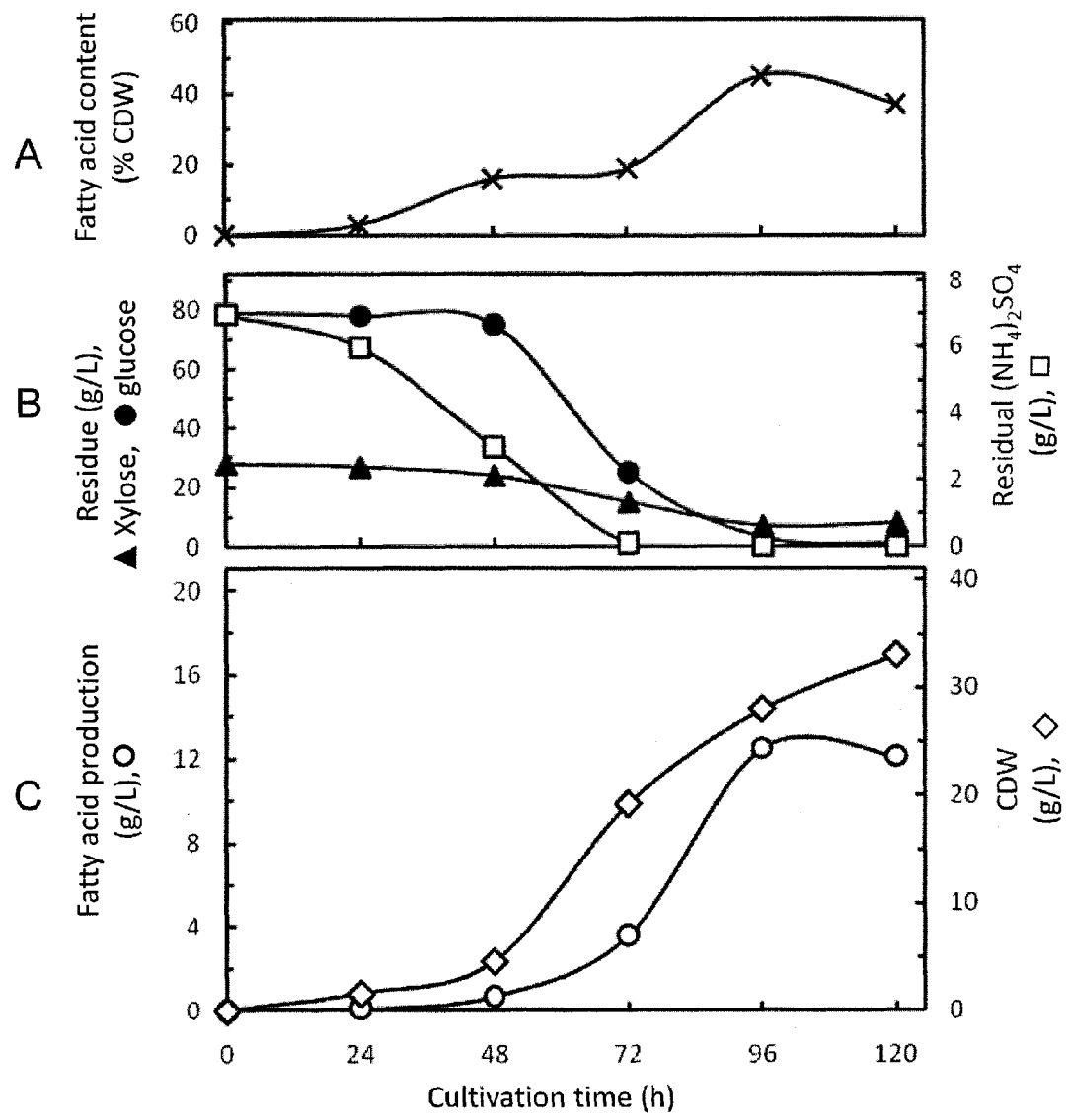
FIGS. 10A-10C show graphs depicting lipid production in *Rhodococcus opacus* bacterial strain MITXM-61 using a saccharified corn stover solution, in a bioreactor, as a function of time.

The cell growth increased after 48 h of cultivation and maximum fatty acid accumulation of 12.5 g/L, representing 45% of CDW, was obtained during the stationary phase, 96 h post-inoculation, concomitant with the complete consumption of the glucose/xylose in the medium (FIGS. 10A-10C).

Example 8

Triacylglyceride Production by MITXM-61 Grown in Saccharified Corn Stover Solution from Example 7

Figure 11:
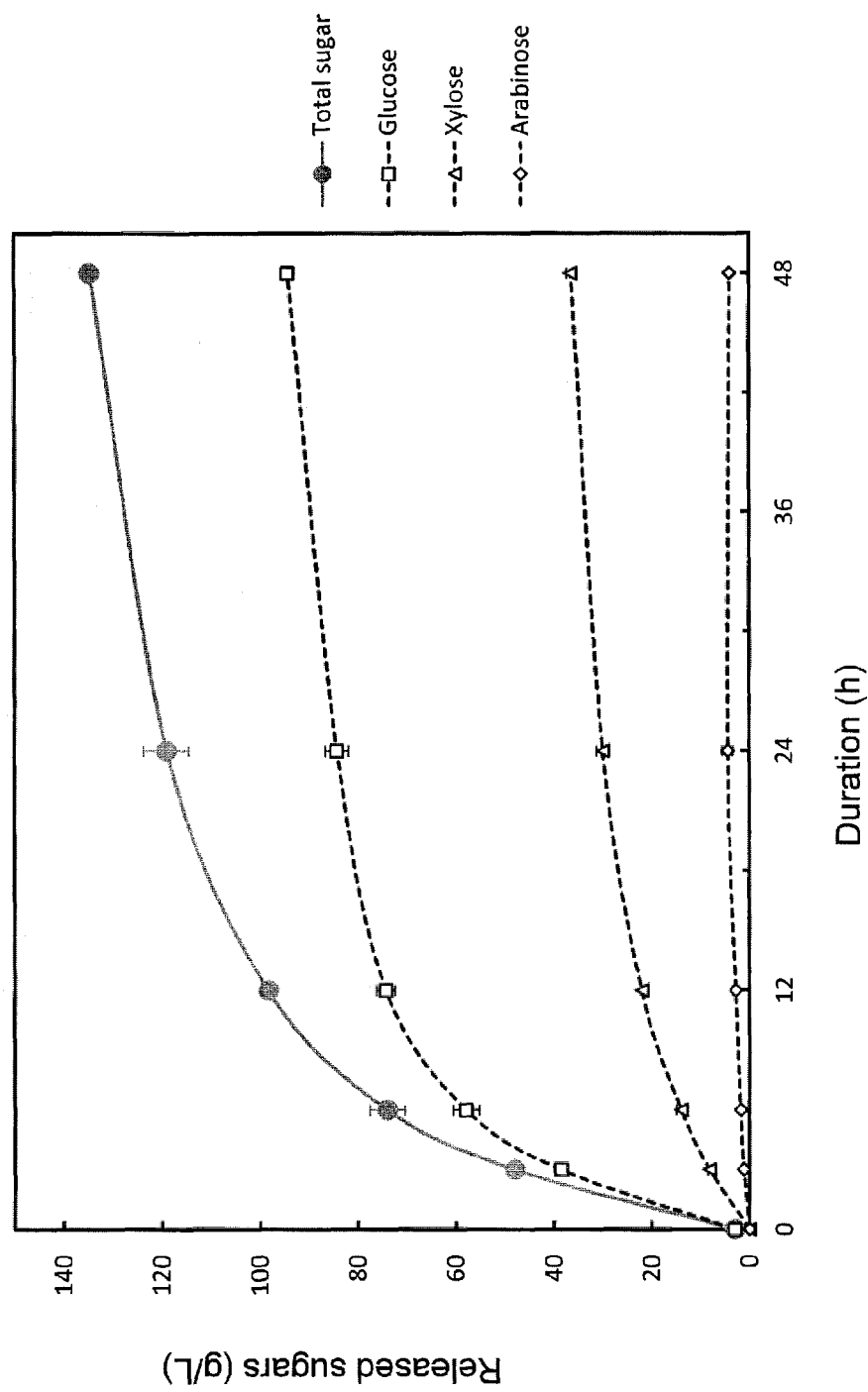
FIG. 11 shows a graph depicting enzymatic saccharification of pretreated corn stover silage as a function of time.

Pretreated material (100 g) was suspended in 890 ml of 0.002N HCl. Ten grams (10 g) of the enzyme (CTec2, Novozymes) was added to the suspension and adjusted to pH 5.0 and 1000 ml in volume. The reaction was carried out at 45° C. for 48 h with 200 rpm agitation. After 3 h and 6 h of incubation, additional pretreated material (50 g each) was added twice. FIG. 11 shows a graph depicting enzymatic saccharification of pretreated corn stover silage.

Figure 12:
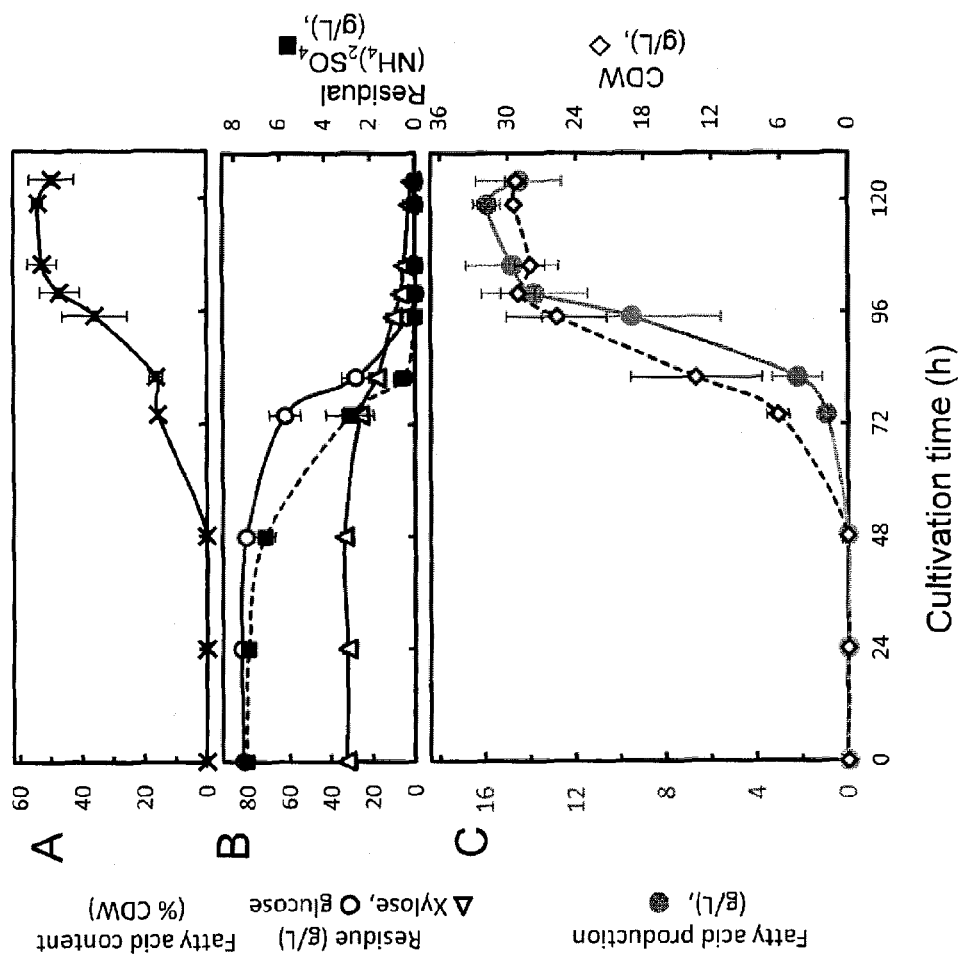
FIGS. 12A-12C show graphs depicting lipid production in *Rhodococcus opacus* bacterial strain MITXM-61 using a saccharified corn stover solution, in a bioreactor, as a function of time.

FIGS. 12A-12C show the time course of lipid production using the saccharified solution. MITXM-61 was grown in the saccharified solution of 118 g/L of initial total sugar composed of 82 g/L glucose, 32 g/L xylose, and 4 g/L arabinose supplemented with 6.7 g/L ammonium sulfate in Bioengineering bioreactors. After 72 h of cultivation, the strain began to produce TAGs. The maximum fatty acid production was 15.9 g/L (54% CDW) after 119 h of cultivation. The productivity was 3.21 g/L/day. The lag phase in the saccharified solution was longer than that in a refined sugar solution containing a similar sugar concentration and composition—a mixture of 80 g/L glucose and 40 g/L xylose, 120 g/L of total sugars. However, the maximum fatty acid production (15.9 g/L) using the saccharified solution was the same in comparison with that (15.9 g/L) in the refined sugar solution. Xylose and glucose in the solution were consumed simultaneously, and xylose was not detected in the medium after 124 h of cultivation. These data demonstrated that MITXM-61 also has the capability of producing large amounts of TAGs when grown on the saccharified corn stover silage solutions containing high sugar concentrations.

Example 9

Triacylglyceride Production by MITXM-61 Grown in Saccharified Sorghum Solution

Figure 13:
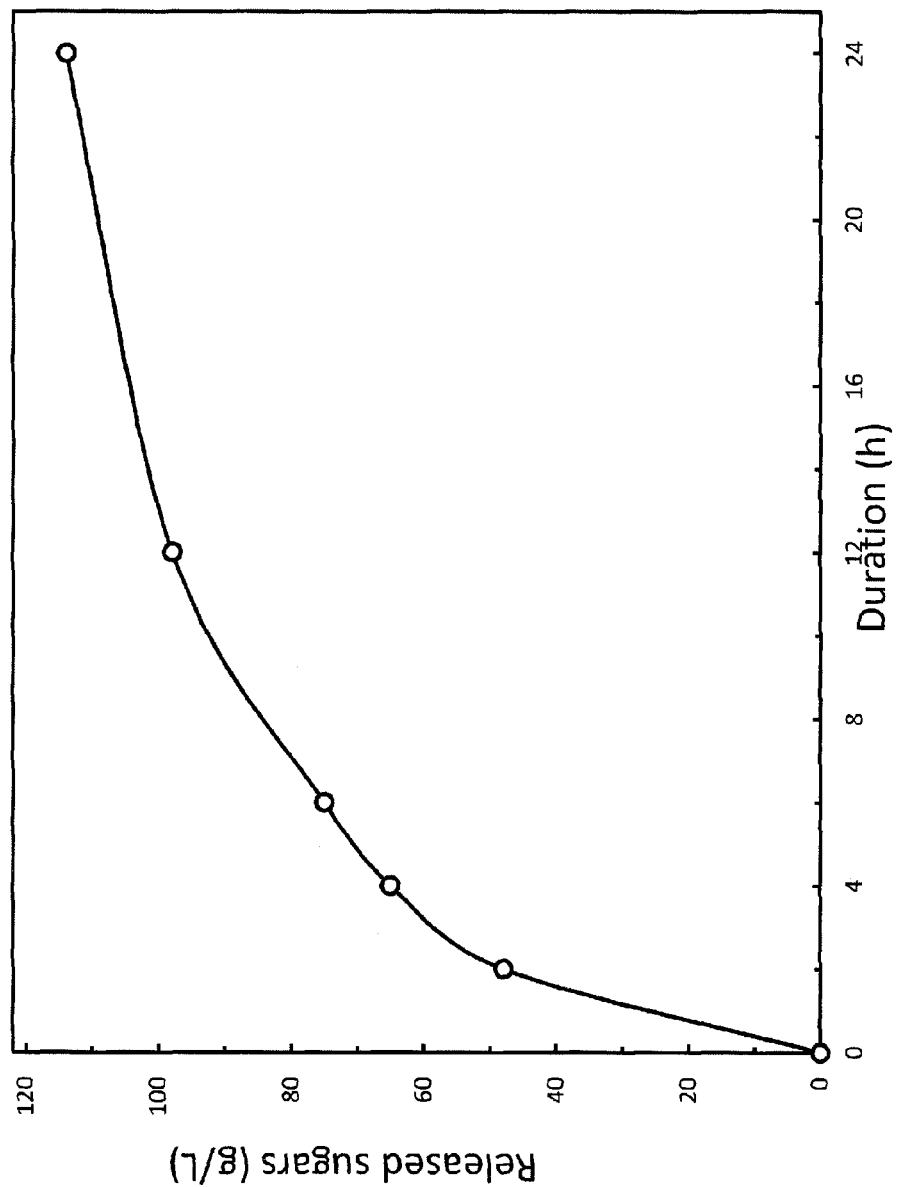
FIG. 13 shows a graph depicting enzymatic saccharification of pretreated sorghum silage as a function of time.

Energy sorghum silage (EX-390) was used as a substrate in this example. The material was pretreated using the method described in Example 6. Five hundred grams of sorghum silage (140 g dry basis) was suspended in 2.5 liters of 1% (w/w) NaOH and heated at 90° C. After 45 min of incubation, the material was filtered, resuspended in 2.5 liters of a fresh 1% NaOH, and kept at 90° C. for 45 min. The slurry was filtered, and the residue was washed three times with 2.5 liters of water. The washed material was dried at 60° C. overnight in an oven and ground into fine particles by a grinder. Seventy-eight grams of the pretreated material were obtained as a fibrous powder. The pretreated material (30 g) was suspended in 246 ml of 0.003 N HCl, and 15.0 ml OPTIMASH® XL (GENENCOR®, Danisco US, Inc.), 6 ml CELLUCLAST® (Novozymes), and 3 ml ACCELLERASE 1500® (GENENCOR®, Danisco US, Inc.) were added to the suspension. The suspension was adjusted to pH 5.0 with 0.1N HCl. The reaction was carried out at 200 rpm and 45° C. After 2, 4, and 6 h of incubation, 10 g of the pretreated material was suspended into the solution (a total of 30 g additional pretreated material). After 24 h of incubation, the saccharified solution contained 114 g/L of total sugars, including 76 g/L glucose, 33 g/L xylose, and 5 g/L of other sugars, and was used for fermentation of MITXM-61. FIG. 13 shows a graph depicting enzymatic saccharification of the pretreated sorghum silage.

MITXM-61 cultivation was performed using a SIX-FORS® bioreactor system (Infors AG CH-4103, Bottmingen, Switzerland) at 30° C. A loopful of MITXM-61 cells grown on a LB agar plate at 30° C. for 3 days was inoculated into 100 ml of a defined medium with 12 g/L glucose, 6 g/L xylose and 1.1 g/L $(NH_4)_2SO_4$ in a 500-ml baffled flask. The culture was incubated on a rotary shaker (200 rpm) at 30° C. for 2 days and the cell density was 16.2 of $OD_{660}$. An aliquot of 20 ml of the broth containing cells was transferred into a 500 ml fermentor vessel containing 180 ml of the saccharified corn stover solution and 20 ml of supplement solution with 1.1 g $(NH_4)_2SO_4$, 0.6 g $MgSO_4.7H_2O$, 0.009 g $CaCl_2.2H_2O$, 0.6 ml trace element solution, 0.6 ml stock A solution, and 3.52 ml 1 M phosphate buffer. The pH value in the medium was maintained at 6.9±0.1 by the addition of 2 M NaOH. Dissolved oxygen was measured with an Ingold polarographic probe and maintained at above 60% $O_2$ saturation by adjusting the agitation speed up to 1000 rpm, and by automatically adjusting the mixture of air and pure oxygen flow via flow controllers while maintaining air gas flow at 1.0 VVM. When it is necessary to prevent foam formation, polypropylene glycol P 2000 (Fluka) was manually added to each vessel.

Figure 14:
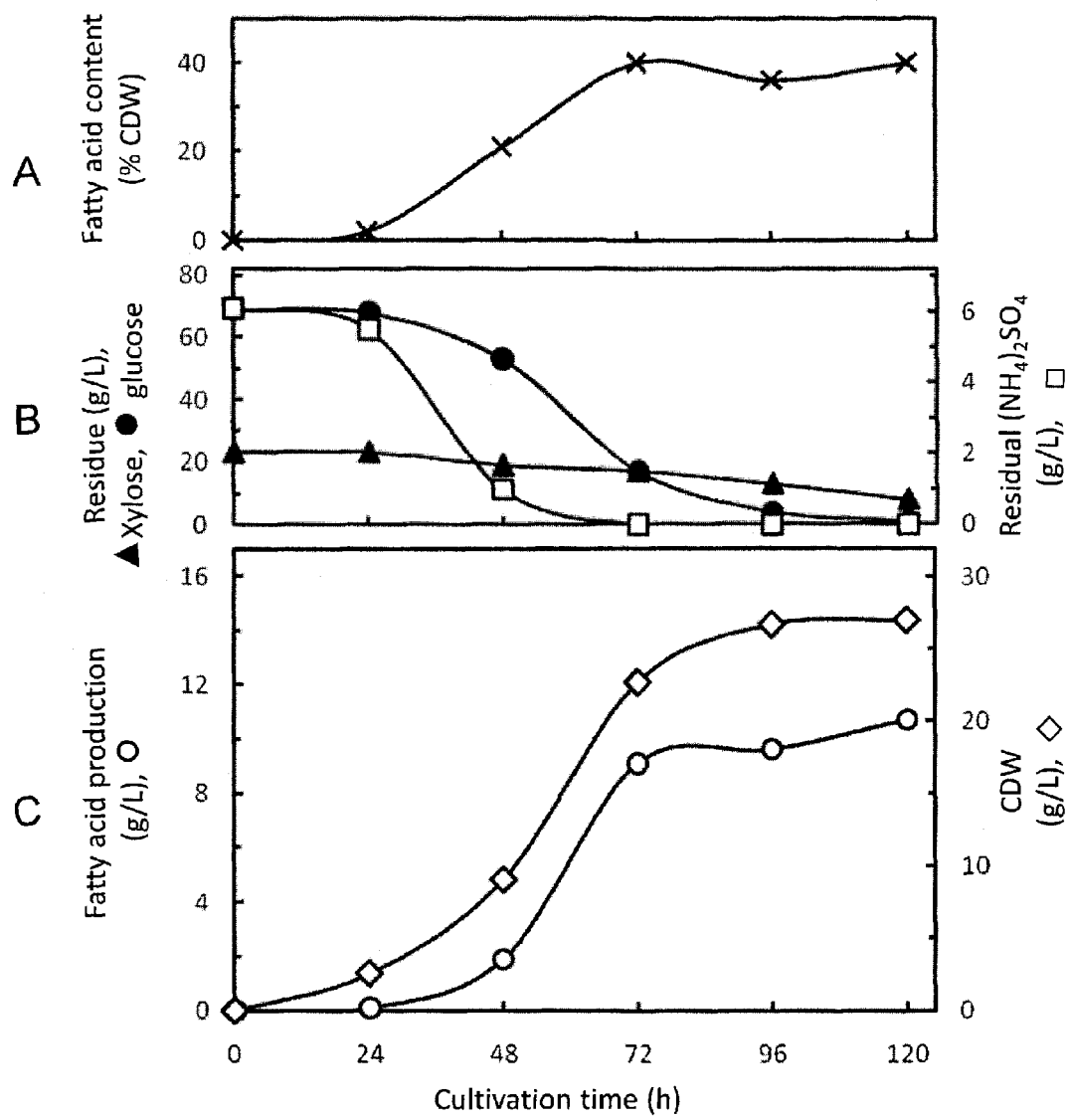
FIGS. 14A-14C show graphs depicting lipid production in *Rhodococcus opacus* bacterial strain MITXM-61 using a saccharified sorghum solution, in a bioreactor, as a function of time.
Figure 15:
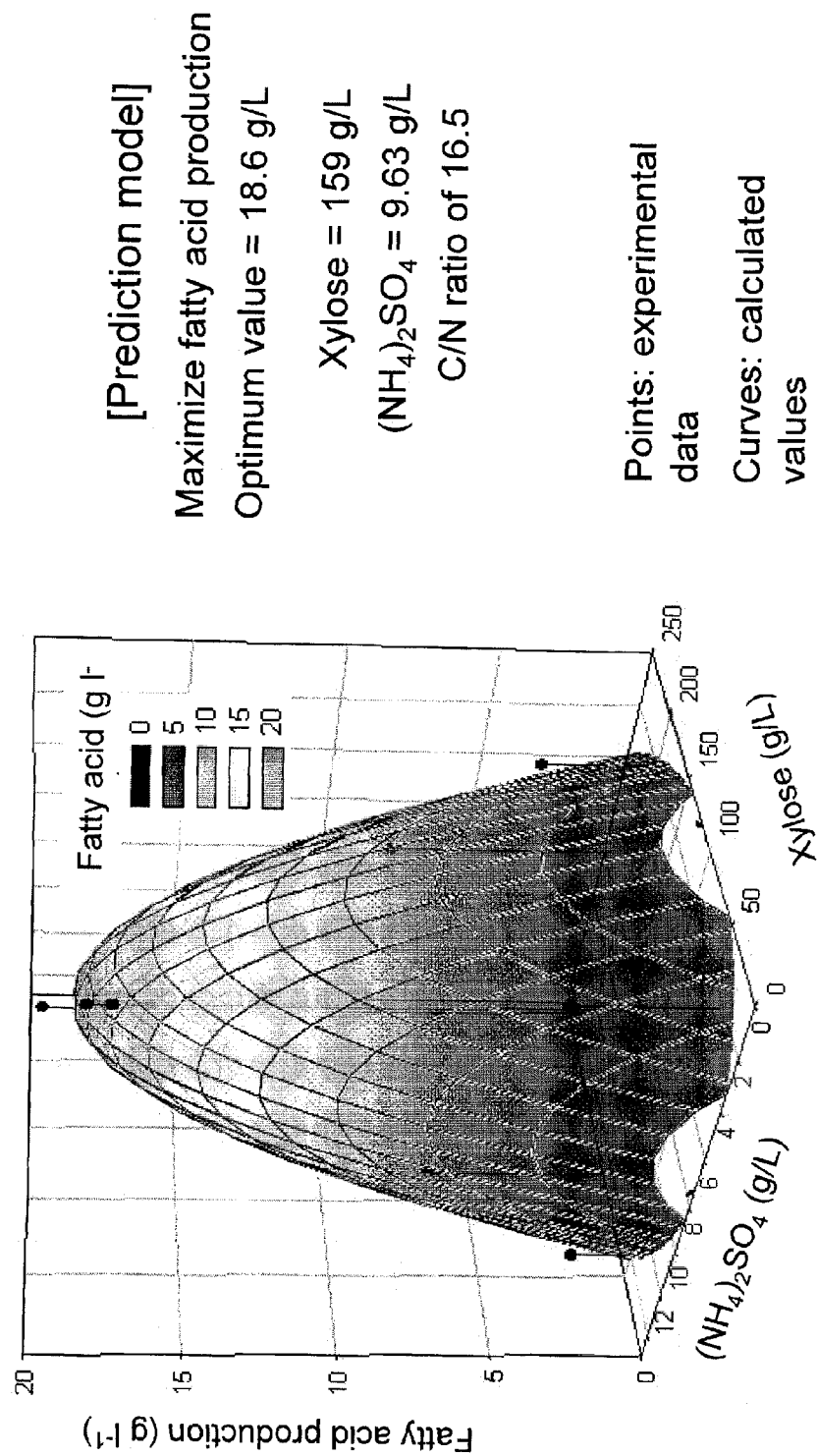
FIG. 15 shows a graph of a response surface plot of the effect of xylose and ammonium sulfate concentrations on lipid production. To optimize MITXM-61 lipid production on xylose, a response surface methodology was used. MITXM-61 was found to grow and accumulate triacylglycerides (TAGs) at a concentration of 240 g/L xylose. When the strain is grown in a defined medium with a C/N ratio of 16.5 containing 159 g/L xylose and 9.63 g/L ammonium sulfate, a maximal production of 18.6 g/L fatty acids is predicted.

The cell growth increased after 24 h of cultivation and maximum fatty acid accumulation of 10.7 g/L, representing 40%, of CDW, was obtained during the stationary phase, 120 h post-inoculation, concomitant with the complete consumption of the glucose/xylose in the medium (FIG. 14).

Example 10

TAGs from Culture Media Containing Various Sugar Compositions

Table III shows fatty acid composition profiles as a percentage of total fatty acid of R. opacus TAGs from culture media containing various sugar compositions. R. opacus was grown in saccharified corn stover silage solution containing 118 g/L of total sugar, defined medium containing 120 g/L of xylose, 40 g/L of xylose, and 80 g/L of glucose, or 120 g/L of glucose. The wild type PD630 strain was grown in defined medium with glucose alone and MITXM-61. The xylose-fermenting strain was grown in the saccharified solution, xylose only, and xylose/glucose mix. These results were analyzed when fatty acid production in each condition reached its maximum state. The cultivation time for obtaining the maximum fatty acid production varied from 72 h to 144 h. The maximum fatty acid production among these four conditions was in the range of 14.9 to 17.4 g/L, which was almost the same level. Fatty acid profiles under these conditions were very similar. The accumulated fatty acids consisted primarily of palmitic acid (28% to 33%), oleic acid (21% to 26%) and cis-10-heptadecenoic acid (13% to 17%).

TABLE III

| Fatty acid species | Saccharified solution Cellulosic sugars[1] | Defined medium Xylose[2] | Xylose/Glucose[3] | Glucose[4] |
|---|---|---|---|---|
| Myristic acid (C14:0) | 2.0 (±0.00) | 1.3 (±1.05) | 2.1 (±0.45) | 2.0 (±0.07) |
| Pentadecanoic acid (C15:0) | 5.0 (±0.00) | 4.8 (±0.27) | 5.5 (±0.24) | 7.4 (±1.29) |
| Palmitic acid (C16:0) | 29.7 (±0.58) | 30.3 (±0.60) | 32.7 (±1.93) | 27.8 (±0.06) |
| Palmitoleic acid (C16:1) | 9.7 (±0.58) | 9.2 (±0.29) | 10.9 (±0.72) | 10.7 (±0.04) |
| Heptadecanoic acid (C17:0) | 9.0 (±0.00) | 9.7 (±0.27) | 8.5 (±0.53) | 10.2 (±0.04) |
| cis-10-Heptadecenoic acid (C17:1) | 14.7 (±0.58) | 13.1 (±0.32) | 13.2 (±0.88) | 17.2 (±0.88) |
| Stearic acid (C18:0) | 5.0 (±0.00) | 6.1 (±0.72) | 6.4 (±0.79) | 4.1 (±0.52) |
| Oleic acid (C18:1) | 24.3 (±0.58) | 25.5 (±0.72) | 20.5 (±3.30) | 20.7 (±2.82) |
| Strain | MITXM-61 | MITXM-61 | MITXM-61 | PD630 |
| Cultivation time (h) | 119 | 144 | 72 | 96 |
| Fatty acid production (g l$^{-1}$) | 15.9 (±0.60) | 14.9 (±0.15) | 15.9 (±1.19) | 17.4 (±0.24) |

Equivalents And Scope

Those skilled in the art will recognize or be able to ascertain using no more than routine experimentation many equivalents to the specific embodiments described herein.

In the claims articles such as "a," "an," and "the" may mean one or more (at least one) than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, some embodiments of the invention or aspects of the invention consist, or consist essentially of, such elements and/or features. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

As used herein, the term "about" generally may refer to any value within a range of 10% of the recited value. In some instance, however, "about" may encompasses a range of 20% of the recited value.

In addition, it is to be understood that any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the methods of the invention can be excluded from any one or more claims, for any reason, whether or not related to the existence of prior art. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Each of the foregoing patents, patent applications and references is hereby incorporated by reference, particularly for the teaching referenced herein.

What is claimed is:

1. A method of producing triacylglycerides, the method comprising:

culturing in liquid culture medium containing xylose, mutant xylose-fermenting *Rhodococcus opacus* bacterial cells that metabolize xylose for a time sufficient to produce triacylglycerides; and collecting the cell culture medium, or isolating the triacylglycerides, from the cell culture medium, wherein the mutant xylose-fermenting *Rhodococcus opacus* bacterial cells do not express an exogenous xylose-metabolism gene.

2. The method of claim 1, wherein the xylose is obtained from renewable biomass.

3. The method of claim 1, wherein the mutant xylose-fermenting *Rhodococcus opacus* bacterial cells are *Rhodococcus opacus* bacterial strain MITXM-61 cells, deposited with the ATCC® Patent Depository on Oct. 26, 2011, and having the deposit number PTA-12196.

4. A method comprising isolating triacylglycerides from a culture of mutant xylose-fermenting *Rhodococcus opacus* bacterial cells that have metabolized xylose in the culture medium, wherein the mutant xylose-fermenting *Rhodococcus opacus* bacterial cells do not express an exogenous xylose-metabolism gene.

5. The method of claim 1, wherein the mutant xylose-fermenting *Rhodococcus opacus* bacterial cells are spontaneous mutant bacterial cells.

6. The method of claim 1, wherein the mutant xylose-fermenting *Rhodococcus opacus* bacterial cells express at least one native, cryptic xylose-metabolism gene.

7. The method of claim 1, wherein the mutant xylose-fermenting *Rhodococcus opacus* bacterial cells produce triacylglycerides in the absence of an antibiotic.

8. The method of claim 4, wherein the mutant xylose-fermenting *Rhodococcus opacus* bacterial cells are *Rhodococcus opacus* bacterial strain MITXM-61 cells, deposited with the ATCC® Patent Depository on Oct. 26, 2011, and having the deposit number PTA-12196.

9. The method of claim 4, wherein the culture medium comprises about 5 g/L to about 240 g/L of xylose.

10. The method of claim 4, wherein the triacylglycerides are produced in an amount of about 14 g/L to about 16 g/L of culture medium.

11. The method of claim 4, wherein the amount of triacylglycerides produced during stationary phase of growth of the bacterial cells is at least 40 % of the bacterial cell dry weight, at least 50 % of the bacterial cell dry weight, or at least 60 % of the bacterial cell dry weight.

12. The method of claim 4, wherein the culture medium further comprises glucose.

13. The method of claim 4, wherein the culture medium is not supplemented with a xylose metabolism enzyme.

14. The method of claim 4, wherein the culture medium comprises xylose obtained from a lignocellulose biomass.

15. The method of claim 4, wherein the culture medium does not comprise fermentation inhibitors.

16. The method of claim 1, wherein the mutant xylose-fermenting *Rhodococcus opacus* cells are mutant xylose-fermenting *Rhodococcus opacus* PD630 cells.

17. The method of claim 4, wherein the culture medium comprises xylose, $(NH_4)_2SO_4$, $MgSO_4.7H_2O$, $CaCl_2.2H_2O$, trace element solution, stock A solution and phosphate buffer.

18. The method of claim 1, wherein the culture medium comprises about 5 g/L to about 240 g/L of xylose.

19. The method of claim 1, wherein the triacylglycerides are produced in an amount of about 14 g/L to about 16 g/L of culture medium.

20. The method of claim 4, wherein the mutant xylose-fermenting *Rhodococcus opacus* bacterial cells are spontaneous mutant bacterial cells.

21. The method of claim 4, wherein the mutant xylose-fermenting *Rhodococcus opacus* bacterial cells express at least one native, cryptic xylose-metabolism gene.

22. The method of claim 4, wherein the mutant xylose-fermenting *Rhodococcus opacus* cells are mutant xylose-fermenting *Rhodococcus opacus* PD630 cells.

\* \* \* \* \*